United States Patent
Gamache et al.

(10) Patent No.: US 12,416,608 B2
(45) Date of Patent: Sep. 16, 2025

(54) ANOMALY DETECTION AND DIAGNOSIS IN CHROMATOGRAPHY APPLICATIONS

(71) Applicant: SPIRA INNOVATION INC., Québec (CA)

(72) Inventors: Yves Gamache, Québec (CA); Andre Lamontagne, Québec (CA)

(73) Assignee: SPIRA INNOVATION INC. (CA)

( * ) Notice: Subject to any disclaimer, the term of this patent is extended or adjusted under 35 U.S.C. 154(b) by 628 days.

(21) Appl. No.: 17/784,887

(22) PCT Filed: Dec. 10, 2020

(86) PCT No.: PCT/CA2020/051703
§ 371 (c)(1),
(2) Date: Jun. 13, 2022

(87) PCT Pub. No.: WO2021/113977
PCT Pub. Date: Jun. 17, 2021

(65) Prior Publication Data
US 2023/0012349 A1    Jan. 12, 2023

Related U.S. Application Data

(60) Provisional application No. 62/947,844, filed on Dec. 13, 2019.

(51) Int. Cl.
*G01N 30/86* (2006.01)
*G01N 30/02* (2006.01)
(Continued)

(52) U.S. Cl.
CPC ......... *G01N 30/8634* (2013.01); *G01N 30/26* (2013.01); *G01N 30/74* (2013.01);
(Continued)

(58) Field of Classification Search
CPC ....... G01N 2030/025; G01N 2030/027; G01N 30/7206; G01N 30/7233; G01N 30/8672;
(Continued)

(56) References Cited

U.S. PATENT DOCUMENTS 5,958,246 A    9/1999   Tipler et al.
2019/0162707 A1*  5/2019   Strauch ................. G01N 30/88

FOREIGN PATENT DOCUMENTS

CN    113167771 B   *  9/2023  ............ G01N 30/46
WO    88/08133 A1    10/1988

OTHER PUBLICATIONS

International Search and Written Opinion mailed Feb. 15, 2021 for corresponding PCT Application No. PCT/CA2020/051703.
(Continued)

*Primary Examiner* — Kristina M Deherrera
*Assistant Examiner* — Truong D Phan
(74) *Attorney, Agent, or Firm* — David Meibos; Maywood IP Law

(57) ABSTRACT

A method for anomaly detection and diagnosis in a chromatography system including a sample handling unit, a chromatographic separation unit, and a detection unit is disclosed. The method can include performing, with the chromatography system, a chromatography analysis of a sample to obtain a chromatogram of the sample, the sample including a known quantity of a reference standard. The method can also include determining peak information corresponding to the reference standard in the chromatogram and determining whether the peak information conforms with an expected response of the chromatography system associated with the reference standard. If the peak information does not conform with the expected response, the method can include determining that there is an anomaly in the operation of the chromatography system and diagnosing
(Continued)

a cause of the anomaly as relating to the operation of at least one the sample handling unit, the chromatographic separation unit, and the detection unit.

40 Claims, 9 Drawing Sheets

(51) Int. Cl.
　　*G01N 30/26*　　　(2006.01)
　　*G01N 30/74*　　　(2006.01)
　　*G01N 30/88*　　　(2006.01)
　　*G01N 33/497*　　(2006.01)
(52) U.S. Cl.
　　CPC ..... *G01N 30/8637* (2013.01); *G01N 30/8665* (2013.01); *G01N 33/497* (2013.01); *G01N 2030/025* (2013.01); *G01N 2030/8813* (2013.01)

(58) Field of Classification Search
　　CPC ........... G01N 33/0006; G01N 33/0008; G01N 33/007; G01N 30/8651; G01N 30/04; G01N 2030/889; G01N 2030/8813; G01N 30/26; G01N 30/74; G01N 30/8634; G01N 30/8637; G01N 30/8658; G01N 30/8665; G01N 33/497
　　USPC ... 73/23.35–23.36, 23.21–23.22, 61.52, 23.3
　　See application file for complete search history.

(56) References Cited

OTHER PUBLICATIONS

Supplementary European Search Report mailed Nov. 17, 2023 for corresponding European Patent Application No. 20899797.

\* cited by examiner

ANOMALY DETECTION AND DIAGNOSIS IN CHROMATOGRAPHY APPLICATIONS

RELATED PATENT APPLICATIONS

The present application is a national stage application under 35 U.S.C. § 371 of International Application No. PCT/CA2020/051703, filed on Dec. 12, 2020, which claims priority to U.S. Provisional Patent Application No. 62/947,844 filed on Dec. 13, 2019. The contents of the above-referenced patent applications are incorporated herein by reference in their entirety.

TECHNICAL FIELD

The technical field generally relates to chromatography, and more particularly, to methods and systems for the detection and diagnosis of anomalous operation in chromatography applications.

BACKGROUND

Chromatography has been used for decades in a wide variety of fields and industries for separating and analyzing constituents of a sample. The sample is typically dissolved or otherwise introduced in a fluid to form a mobile phase, which is carried through a column or another separation device containing a stationary phase. Chromatography can be classified into two main branches: gas chromatography (GC) and liquid chromatography (LC), depending on whether the mobile phase is a gas or a liquid. While passing the mobile phase through the column or separation device, different sample components travel at different speeds due to their different interaction strengths or affinities with the stationary phase, leading to different retention times, with the stronger the interaction, the longer the retention time.

Chromatography systems use columns, valves, pumps, detectors, and other hardware equipment for the temporal separation of a sample into its components and the subsequent detection of the separated components. In order to be accurate and reliable, chromatography systems rely on tight control over many operating parameters and conditions including, but not limited to, carrier fluid flow and purity, column temperature, sample injection volume, inertness of components, and ambient temperature and pressure compensation. The performance of chromatography systems can be impacted by various sources of variation, which can be related to the instrumentation, materials, environmental and processing conditions, and operator errors. For example, column properties can change over time due to aging or pollution from carrier gas or sample contaminants, resulting in retention time drifts, which can cause analytes to be incorrectly detected or not detected at all. Detector response can also change over time, generally by decreasing, due to aging, damage, degradation, and other effects such as electronics and temperature drifts, leading to imprecise and inaccurate measurements. While maintaining accurate and reliable performance is important in any chromatography application, improper operation or faulty analysis can have more severe consequences in some fields, notably in medical diagnosis applications. For example, in the field of exhaled breath analysis using GC for the detection of cancer and other diseases and disorders, a failure to diagnose, a late diagnosis, or a misdiagnosis can have fatal, life-threatening, or disabling health consequences.

Methods exist for obtaining quantitative information from chromatography data for purposes of enhancing system performance, which can be based on normalized peak areas, internal standards, external standards, and standard addition. While these methods may be useful in some applications, they are not without drawbacks and limitations. Therefore, there remains a need for techniques enabling better detection of anomalous or faulty operation in chromatography applications for improved reliability.

SUMMARY

The present description generally relates to techniques for the monitoring, detection, diagnosis, and compensation of anomalies in chromatography applications.

In accordance with an aspect, there is provided a method for anomaly detection and diagnosis in a chromatography system, the chromatography system including a sample handling unit, a chromatographic separation unit, and a detection unit. The method can include:

performing, with the chromatography system, a chromatography analysis of a sample to obtain a chromatogram of the sample, the sample including a known quantity of a reference standard; determining peak information corresponding to the reference standard in the chromatogram of the sample;

determining whether the peak information conforms with an expected overall standard response of the chromatography system associated with the reference standard;

if it is determined that the peak information conforms with the expected overall standard response, determining that there is no anomaly in the operation of the chromatography system; and if it is determined that the peak information does not conform with the expected overall standard response, determining that there is an anomaly in the operation of the chromatography system and diagnosing a cause of the anomaly as relating to at least one of the operation of the sample handling unit, the operation of the chromatographic separation unit, and the operation of the detection unit.

In some embodiments, the method includes a precalibration operation of determining the expected overall standard response In some embodiments, determining whether the peak information conforms with the expected overall standard response includes:

determining, from the peak information, a current overall standard response of the chromatography system associated with the reference standard; and assessing whether the current overall standard response deviates from the expected overall standard response by more than a predetermined threshold.

In some embodiments, the peak information includes a peak area, a peak height, a peak shape, a peak width, a peak signal-to-noise ratio, or a combination thereof.

In some embodiments, diagnosing the cause of the anomaly includes performing at least one of the following three assessment operations:

assessing whether a first current specific standard response of the chromatography system associated with the reference standard and conveying information about the operation of the sample handling unit conforms with a first expected specific standard response associated with the sample handling unit, and if not, determining that the cause of the anomaly is at least partly related to the operation of the sample handling unit;

assessing whether a second current response of the chromatography system associated with the reference standard and conveying information about the operation of the chromatographic separation unit conforms with a second expected specific standard response associated with the chromatographic separation unit, and if not, determining that the cause of the anomaly is at least partly related to the operation of the chromatographic separation unit; and assessing whether a third current response of the chromatography system associated with the reference standard and conveying information about the operation of the detection unit conforms with a third expected specific standard response associated with the detection unit, and if not, determining that the cause of the anomaly is at least partly related to the operation of the detection unit In some embodiments, the method includes a precalibration operation of determining at least one of the first, second, and third expected specific standard responses.

In some embodiments, assessing whether each of the first, second, and third current responses of the chromatography system conforms with a respective one of the first, second, and third expected specific standard responses includes performing a comparison operation based on a respective predetermined threshold. In some embodiments, performing at least one of the assessment operations includes performing all of the three assessment operations. In some embodiments, the three assessment operations may be performed in a sequential manner starting, for example, with the assessment operation associated with the detection unit.

In some embodiments, the reference standard is an internal standard.

In some embodiments, the sample containing the known quantity of the reference standard is a test sample including target analytes.

In some embodiments, the method includes adding the reference standard to the test sample prior to performing the chromatography analysis.

In some embodiments, adding the reference standard to the test sample includes supplying the reference standard in a sample gas matrix or by permeation.

In some embodiments, the target analytes are provided in a sample gas matrix, and wherein the method includes:
  receiving the test sample in a sample trap of the sample handling unit configured for accumulating and concentrating the test sample prior to injection of the test sample into the chromatographic separation unit;
  releasing the sample gas matrix from the sample trap;
  detecting the sample gas matrix released from the sample trap and generating therefrom a detection signal; and
  analyzing the detection signal to determine information conveying a volume of the test sample injected into the chromatographic separation unit.

In some embodiments, the test sample is an exhaled breath sample. In some embodiments, the method includes collecting, at a sample collector of the sample handling unit, the exhaled breath sample via exhalation by a user.

In some embodiments, the method includes analyzing the chromatogram of the sample to perform identification and quantification of the target analytes.

In some embodiments, the sample containing the known quantity of the reference standard is a standard sample, and wherein the method includes:
  performing, with the chromatography system, and before or after the chromatography analysis of the standard sample, a chromatography analysis of a test sample to obtain a chromatogram of the test sample, the test sample including target analytes; and
  analyzing the chromatogram of the sample to perform identification and quantification of the target analytes.

In some embodiments, the reference standard has a same composition as one of the target analytes of the test sample. In some embodiments, the test sample is an exhaled breath sample. In some embodiments, the reference standard includes benzene, styrene, toluene, hydrogen sulfide, or a combination thereof.

In some embodiments, the method includes collecting, at a sample collector of the sample handling unit, the exhaled breath sample via exhalation by a user.

In some embodiments, the sample handling unit includes a sample conditioner configured for conditioning the sample prior to injection of the sample into the chromatographic separation unit, and the method includes:
  flowing purified gas through the sample conditioner;
  detecting the purified gas after the purified gas exits the sample conditioner
  generating, from the detected purified gas, a purified gas detection signal;
  analyzing the purified gas detection signal to assess whether the purified gas detection signal includes a feature indicative of a presence of contaminants in the detected purified gas; and
  if the purified gas detection signal includes such a feature, determining that a leak integrity of the sample conditioner is possibly compromised.

In some embodiments, the method includes generating an alert in response to a determination that there is an anomaly in the operation of the chromatography system. In some embodiments, the alert conveys information relating to the cause of the anomaly.

In some embodiments, the method includes taking a corrective action to correct, at least partly, the anomaly. In some embodiments, taking the corrective action includes implementing the corrective action automatically.

In some embodiments, if it is determined that the anomaly originates at least partly from the sample handling unit, applying the corrective action at least partly to the sample handling unit; if it is determined that the anomaly originates at least partly from the chromatographic separation unit, applying the corrective action at least partly to the chromatographic separation unit; and if it is determined that the anomaly originates at least partly from the detection, applying the corrective action at least partly to the detection unit.

In some embodiments, the method includes verifying an effect of the corrective action on the operation of the chromatography system.

In some embodiments, verifying the effect of the corrective action includes:
  determining a corrected overall standard response using the same or another sample; and assessing whether the corrected overall standard response conforms with the expected overall standard response.

In some embodiments, the detection unit includes a plasma emission detector.

In some embodiments, the chromatography system is a gas chromatography system, and the sample is a gas sample.

In some embodiments, the chromatography system includes a carrier gas unit, and wherein the method includes:
  supplying a flow of carrier gas from the carrier gas unit;
  introducing the flow of carrier gas with the gas sample to form a mobile for injection into the chromatographic separation unit.

In some embodiments, the method includes recycling at least part of the carrier gas after performing the chromatography analysis.

In some embodiments, the sample handling unit includes a sample injector configured for injecting the sample into the chromatographic separation unit, and wherein the method includes: circulating purge gas through the sample injector;
- detecting the purge gas after the purge gas exits the sample injector
- generating, from the detected purge gas, a purge gas detection signal;
- analyzing the purge gas detection signal to assess whether the purge gas detection signal includes a feature indicative of a presence of contaminants in the detected purge gas; and
- if the purge gas detection signal includes such a feature, determining that a leak integrity of the sample injector is possibly compromised.

In accordance with another aspect, there is provided a chromatography system for performing a chromatography analysis of a sample including a known quantity of a reference standard. The chromatography system can include:
- a sample handling unit configured to process the sample;
- a chromatographic separation unit configured to receive the sample from the sample handling unit and to perform a chromatographic separation of the sample;
- a detection unit configured to detect the chromatographically separated sample and generate therefrom a detection signal;
- a control and processing unit configured to:
  - receive the detection signal from the detection unit;
  - obtain a chromatogram of the sample from the detection signal;
  - determine peak information corresponding to the reference standard in the chromatogram of the sample;
  - determine whether the peak information conforms with an expected overall standard response of the chromatography system associated with the reference standard;
  - if it is determined that the peak information conforms with the expected overall standard response, determine that there is no anomaly in the operation of the chromatography system; and
  - if it is determined that the peak information does not conform with the expected overall standard response, determine that there is an anomaly in the operation of the chromatography system and diagnose a cause of the anomaly as relating to at least one of the operation of the sample handling unit, the operation of the chromatographic separation unit, and the operation of the detection unit.

In some embodiments, the control and processing unit is configured to determine whether the peak information conforms with the expected overall standard response by:
- determining, from the peak information, a current overall standard response of the chromatography system associated with the reference standard; and
- assessing whether the current overall standard response deviates from the expected overall standard response by more than a predetermined threshold.

In some embodiments, the control and processing unit is configured to diagnose the cause of the anomaly by performing at least one of the following three assessment operations:
- assessing whether a first current specific standard response of the chromatography system associated with the reference standard and conveying information about the operation of the sample handling unit conforms with a first expected specific standard response associated with the sample handling unit, and if not, determining that the cause of the anomaly is at least partly related to the operation of the sample handling unit;
- assessing whether a second current response of the chromatography system associated with the reference standard and conveying information about the operation of the chromatographic separation unit conforms with a second expected specific standard response associated with the chromatographic separation unit, and if not, determining that the cause of the anomaly is at least partly related to the operation of the chromatographic separation unit; and
- assessing whether a third current response of the chromatography system associated with the reference standard and conveying information about the operation of the detection unit conforms with a third expected specific standard response associated with the detection unit, and if not, determining that the cause of the anomaly is at least partly related to the operation of the detection unit.

In some embodiments, the control and processing unit is configured to assess whether the first, second, and third current responses of the chromatography system respectively conform with the first, second, and third expected specific standard responses by performing a comparison operation based on a respective predetermined threshold.

In some embodiments, the control and processing unit is configured to perform the three assessment operations.

In some embodiments, the sample containing the known quantity of the reference standard is a test sample including target analytes, and wherein the sample handling unit includes a sample collector configured to collect the test sample. In some embodiments, the test sample is an exhaled breath sample, and wherein the sample collector is configured to receive the exhaled breath sample via exhalation by a user. In some embodiments, the sample handling unit is configured to add the reference standard to the test sample.

In some embodiments, the control and processing unit is configured to analyze the chromatogram of the sample to perform identification and quantification of the target analytes.

In some embodiments, the control and processing unit is configured to generate an alert in response to a determination that there is an anomaly in the operation of the chromatography system. In some embodiments, the alert conveys information relating to the cause of the anomaly.

In some embodiments, the control and processing unit is configured to determine a corrective action to correct, at least partly, the anomaly. In some embodiments, the control and processing unit is configured to verifying an effect of the corrective action on the operation of the chromatography system.

In some embodiments, the control and processing unit is configured to verify the effect of the corrective action by:
- determining a corrected overall standard response using the same or another sample; and
- assessing whether the corrected overall standard response conforms with the expected overall standard response.

In some embodiments, the detection unit includes a plasma emission detector.

In some embodiments, the chromatography system is a gas chromatography system. In some embodiments, the chromatography system includes a carrier gas unit configured to supplying a flow of carrier gas and introduce the flow of carrier gas with the gas sample to form a mobile for injection into the chromatographic separation unit. In some embodiments, the chromatography system includes a carrier gas recycling unit configured to recycle at least part of the carrier gas used to perform the chromatography analysis.

In accordance with another aspect, there is provided a non-transitory computer readable storage medium having stored thereon computer readable instructions that, when executed by a processor, cause the processor to perform a method for anomaly detection and diagnosis in a chromatography system configured for obtaining a chromatogram of a sample including a known quantity of a reference standard, the chromatography system including a sample handling unit, a chromatographic separation unit, and a detection unit. The method can include:
- providing the chromatogram of the sample;
- determining peak information corresponding to the reference standard in the chromatogram of the sample;
- determining whether the peak information conforms with an expected overall standard response of the chromatography system associated with the reference standard;
- if it is determined that the peak information conforms with the expected overall standard response, determining that there is no anomaly in the operation of the chromatography system; and
- if it is determined that the peak information does not conform with the expected overall standard response, determining that there is an anomaly in the operation of the chromatography system and diagnosing a cause of the anomaly as relating to at least one of the operation of the sample handling unit, the operation of the chromatographic separation unit, and the operation of the detection unit.

In some embodiments, the method includes determining the expected overall standard response via a precalibration operation.

In some embodiments, determining whether the peak information conforms with the expected overall standard response includes:
- determining, from the peak information, a current overall standard response of the chromatography system associated with the reference standard; and
- assessing whether the current overall standard response deviates from the expected overall standard response by more than a predetermined threshold.

In some embodiments, diagnosing the cause of the anomaly includes performing at least one of the following three assessment operations:
- assessing whether a first current specific standard response of the chromatography system associated with the reference standard and conveying information about the operation of the sample handling unit conforms with a first expected specific standard response associated with the sample handling unit, and if not, determining that the cause of the anomaly is at least partly related to the operation of the sample handling unit;
- assessing whether a second current response of the chromatography system associated with the reference standard and conveying information about the operation of the chromatographic separation unit conforms with a second expected specific standard response associated with the chromatographic separation unit, and if not, determining that the cause of the anomaly is at least partly related to the operation of the chromatographic separation unit; and
- assessing whether a third current response of the chromatography system associated with the reference standard and conveying information about the operation of the detection unit conforms with a third expected specific standard response associated with the detection unit, and if not, determining that the cause of the anomaly is at least partly related to the operation of the detection unit.

In some embodiments, the method includes determining at least one of the first, second, and third expected specific standard responses via a precalibration operation.

In some embodiments, assessing whether each of the first, second, and third current responses of the chromatography system conforms with a respective one of the first, second, and third expected specific standard responses includes performing a comparison operation based on a respective predetermined threshold. In some embodiments, performing at least one of the assessment operations includes performing all of the three assessment operations.

In some embodiments, the reference standard is an internal standard.

In some embodiments, the sample containing the known quantity of the reference standard is a test sample including target analytes. In some embodiments, the test sample is an exhaled breath sample.

In some embodiments, the method includes analyzing the chromatogram of the sample to perform identification and quantification of the target analytes.

In some embodiments, the method includes generating an alert in response to a determination that there is an anomaly in the operation of the chromatography system. In some embodiments, the alert conveys information relating to the cause of the anomaly.

In some embodiments, the method includes determining a corrective action to correct, at least partly, the anomaly. In some embodiments, if it is determined that the anomaly originates at least partly from the sample handling unit, the method includes applying the corrective action at least partly to the sample handling unit; if it is determined that the anomaly originates at least partly from the chromatographic separation unit, the method includes applying the corrective action at least partly to the chromatographic separation unit; and if it is determined that the anomaly originates at least partly from the detection, the method includes applying the corrective action at least partly to the detection unit.

In some embodiments, the method includes verifying an effect of the corrective action on the operation of the chromatography system.

In some embodiments, verifying the effect of the corrective action includes:
- determining a corrected overall standard response using the same or another sample; and
- assessing whether the corrected overall standard response conforms with the expected overall standard response.

In accordance with another aspect, there is provided a computer device including a processor; and a non-transitory computer readable storage medium such as disclosed herein, the non-transitory computer readable storage medium being operatively coupled to the processor.

In accordance with another aspect, there is provided a method for anomaly detection and diagnosis in a chromatography system, the chromatography system including a sample handling unit, a chromatographic separation unit, and a detection unit. The method can include:

performing, with the chromatography system, a chromatography analysis of a sample to obtain a chromatogram of the sample, the sample including a known quantity of a reference standard;

detecting a peak corresponding to the reference standard in the chromatogram of the sample;

determining whether the peak corresponding to the reference standard in the chromatogram of the sample conforms with an expected overall standard response of the chromatography system associated with the reference standard; and if it is determined that the peak does not conform with the expected overall standard response, determining that there is an anomaly in the operation of the chromatography system and diagnosing a cause of the anomaly by performing at least one of the following steps:

assessing whether a first current response of the chromatography system associated with the reference standard and conveying information about the operation of the sample handling unit conforms with a first expected specific standard response, and if not, determining that the cause of the anomaly is at least partly related to the operation of the sample handling unit;

assessing whether a second current response of the chromatography system associated with the reference standard and conveying information about the operation of the chromatographic separation unit conforms with a second expected specific standard response, and if not, determining that the cause of the anomaly is at least partly related to the operation of the chromatographic separation unit; and assessing whether a third current response of the chromatography system associated with the reference standard and conveying information about the operation of the detection unit conforms with a third expected specific standard response, and if not, determining that the cause of the anomaly is at least partly related to the operation of the detection unit.

In some embodiments, the method can include a precalibration step of determining the expected overall standard response and the first, second, and third expected specific standard responses.

In some embodiments, determining whether the peak conforms with the expected overall standard response includes a step of determining, from the peak, a current overall standard response of the chromatography system associated with the reference standard, followed by a step of assessing whether the current overall standard response deviates from the expected overall standard response stored in memory by more than a predetermined threshold.

In some embodiments, the assessment of whether the first, second, and third current responses of the chromatography system respectively conform with the first, second, and third expected specific standard responses involves, in each case, a comparison against a respective predetermined threshold.

In some embodiments, the sample containing the known quantity of the reference standard is an unknown test sample including target analytes to be analyzed. The unknown test sample can be an exhaled breath sample. In one variant, the method can include a step of analyzing the chromatogram of the unknown test sample to perform identification and quantification of the target analytes.

In some embodiments, the sample containing the known quantity of the reference standard is a standard sample. In one variant, the method can include a step of performing, with the chromatography system, and before or after the chromatography analysis of the standard sample, a chromatography analysis of an unknown test sample to obtain a chromatogram of the unknown test sample, the unknown test sample including target analytes to be analyzed. For example, the unknown test sample can be an exhaled breath sample. In one variant, the method can include a step of analyzing the chromatogram of the unknown test sample to perform identification and quantification of the target analytes.

In some embodiments, the chromatography system is a gas chromatography system. In another embodiment, the chromatography system is a liquid chromatography system.

In some embodiments, the method can include generating an alert in response to the determination that there is an anomaly in the operation of the chromatography system. The alert generated can convey information about the cause of the anomaly, and can include a request or a recommendation to perform one or more actions. Non-limiting examples of such actions may be related to maintenance, cleaning, repair, replacement, inspection, testing, recalibration, change of operating regime, or any combination thereof.

In some embodiments, the method can include a step of taking a corrective action for attempting to correct, at least partly, the anomaly. Depending on the application, the chromatography system may be configured to implement the corrective action automatically, possibly in real-time, or only upon user authorization. If it is determined that the detected anomaly originates at least partly from the sample handling unit, or at least partly from the chromatographic separation unit, or at least partly from the detection unit, the corrective action can be applied at least partly to the sample handling unit, or at least partly to the chromatographic separation unit, or at least partly to the detection unit, respectively. In one variant, the method can include a step of verifying the effect of the corrective action on the operation of the chromatography system. The verification can include a step of determining a corrected overall standard response using the same or another sample, and assessing whether the corrected overall standard response conforms with the expected overall standard response.

In accordance with an aspect, there is provided a chromatography system configured to perform the method as described herein. The chromatography system can include a sample handling unit, a chromatographic separation unit, a detection unit, and a control and processing unit, which can be configured for performing the chromatography analysis of the sample. The control and processing unit can also be configured for determining whether the peak corresponding to the reference standard in the chromatogram of the sample conforms with the expected overall standard response of the chromatography system associated with the reference standard. If it is determined that the peak does not conform with the expected overall standard response, the control and processing unit can be configured for determining that there is an anomaly in the operation of the chromatography system and for diagnosing a cause of the anomaly by performing at least one of the assessing steps described above.

In accordance with another aspect, there is provided a non-transitory computer readable storage medium having stored thereon computer readable instructions that, when executed by a processor, cause the processor to perform various steps of a method for anomaly detection and diagnosis in a chromatography system, such as described herein.

In accordance with another aspect, there is provided a computer device for use with or in a chromatography system such as described herein, the computer device including a processor and a non-transitory computer readable storage medium operatively coupled to the processor and having stored thereon computer readable instructions that, when executed by a processor, cause the processor to perform various steps of a method for anomaly detection and diagnosis in the chromatography system, such as described herein.

Other method and process steps may be performed prior, during or after the steps described herein. The order of one or more steps may also differ, and some of the steps may be omitted, repeated, and/or combined, as the case may be. In addition, some steps may be performed using various analysis and processing techniques, which may be implemented in hardware, software, firmware, or any combination thereof.

Other objects, features, and advantages of the present description will become more apparent upon reading of the following non-restrictive description of specific embodiments thereof, given by way of example only with reference to the appended drawings. Although specific features described in the above summary and in the detailed description below may be described with respect to specific embodiments or aspects, it should be noted that these specific features may be combined with one another unless stated otherwise.

DETAILED DESCRIPTION

Figure 1:
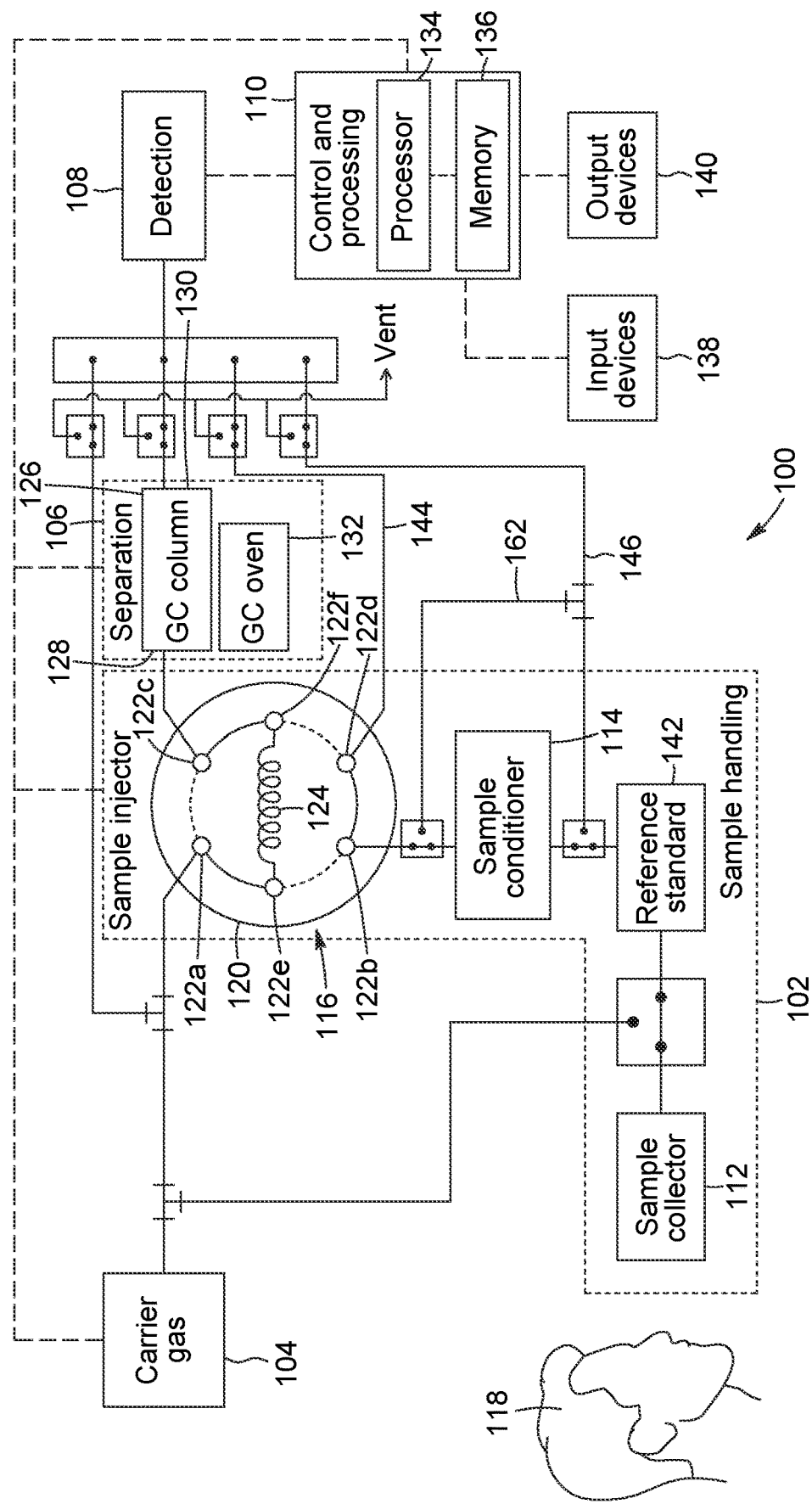
FIG. 1 is a schematic representation of a possible embodiment of a gas chromatography (GC) system.

In the present description, similar features in the drawings have been given similar reference numerals. To avoid cluttering certain figures, some elements may not be indicated if they were already identified in a preceding figure. It should also be understood that the elements of the drawings are not necessarily depicted to scale, since emphasis is placed on clearly illustrating the elements and structures of the present embodiments. Positional descriptors indicating the location and/or orientation of one element with respect to another element are used herein for ease and clarity of description. Unless otherwise indicated, these positional descriptors should be taken in the context of the figures and should not be considered limiting. It is appreciated that such spatially relative terms are intended to encompass different orientations in the use or operation of the present embodiments, in addition to the orientations exemplified in the figures. Furthermore, when a first element is referred to as being "on", "above", "below", "over", or "under" a second element, the first element can be either directly or indirectly on, above, below, over, or under the second element, respectively, such that one or multiple intervening elements may be disposed between the first element and the second element.

The terms "a", "an", and "one" are defined herein to mean "at least one", that is, these terms do not exclude a plural number of elements, unless stated otherwise.

The term "or" is defined herein to mean "and/or", unless stated otherwise.

The expressions "at least one of A, B, and C" and "one or more of A, B, and C", and variants thereof, are understood to include A alone, B alone, and C alone, as well as any combination of A, B, and C.

Terms such as "substantially", "generally", and "about", which modify a value, condition, or characteristic of a feature of an exemplary embodiment, should be understood to mean that the value, condition, or characteristic is defined within tolerances that are acceptable for the proper operation of this exemplary embodiment for its intended application or that fall within an acceptable range of experimental error. In particular, the term "about" generally refers to a range of numbers that one skilled in the art would consider equivalent to the stated value (e.g., having the same or an equivalent function or result). In some instances, the term "about" means a variation of ±10% of the stated value. It is noted that all numeric values used herein are assumed to be modified by the term "about", unless stated otherwise. The term "between" as used herein to refer to a range of numbers or values defined by endpoints is intended to include both endpoints, unless stated otherwise.

The term "based on" as used herein is intended to mean "based at least in part on", whether directly or indirectly, and to encompass both "based solely on" and "based partly on". In particular, the term "based on" may also be understood as meaning "depending on", "representative of", "indicative of", "associated with", and the like.

The terms "match", "matching", and "matched" refer herein to a condition in which two elements are either the same or within some specified tolerance of each other. That is, these terms are meant to encompass not only "exactly" or "identically" matching the two elements but also "substantially", "approximately", or "subjectively" matching the two elements, as well as providing a higher or best match among a plurality of matching possibilities.

The terms "connected" and "coupled", and derivatives and variants thereof, refer herein to any connection or coupling, either direct or indirect, between two or more elements, unless stated otherwise. For example, the connection or coupling between elements may be mechanical, optical, electrical, magnetic, thermal, chemical, logical, fluidic, operational, or any combination thereof.

The term "concurrently" refers herein to two or more processes that occur during coincident or overlapping time periods. The term "concurrently" does not necessarily imply complete synchronicity and encompasses various scenarios including time-coincident or simultaneous occurrence of two processes; occurrence of a first process that both begins and ends during the duration of a second process; and occurrence of a first process that begins during the duration of a second process, but ends after the completion of the second process.

The present description generally relates to techniques for monitoring, detecting, diagnosing, and compensating for improper, anomalous, faulty, or suboptimal operation in chromatography systems and methods. In some implementations, the present techniques can allow the detection and self-diagnosis of anomalies in the operation of a chromatography system to be performed automatically, in real-time, and with limited impact on the total analysis time. In some implementations, the present techniques can involve the monitoring and assessment of one or more response factors associated with a chromatography system.

The term "chromatography" refers herein to an analytical or process technique for separating a sample or mixture into its individual components and analyzing qualitatively and quantitatively the separated sample components. In most chromatography applications, the sample is transported in a carrier fluid to form a mobile phase. Depending on whether the mobile phase is a gas or a liquid, chromatography can be classified into two main branches: gas chromatography (GC) and liquid chromatography (LC), both of which can be used to implement the present techniques. The mobile phase is then carried through a stationary phase, which is located in a column or another separation device. The mobile and stationary phases may be selected so that the components of the sample transported in the mobile phase exhibit different interaction strengths with the stationary phase. This leads to different sample components having different retention times through the system, where the sample components that are strongly interacting with the stationary phase move more slowly with the flow of the mobile phase and elute from the column later than the sample components that are weakly interacting with the stationary phase. As the sample components separate, they elute from the column and enter a detector. The detector is configured to generate an electrical signal whenever the presence of a sample component is detected. The magnitude of the signal is proportional to the concentration level of the detected component. The measurement data can be processed by a computer to obtain a chromatogram, which is a time series of peaks representing the sample components as they elute from the column. The retention time of each peak is indicative of the composition of the corresponding eluting component, while the peak height or area conveys information on the amount or concentration of the eluting component.

The term "sample" refers herein to any substance known, expected, or suspected to contain analytes. Samples can be broadly classified as organic, inorganic, or biological, and can be further subdivided into solids, semi-solids (e.g., gels, creams, pastes, suspensions, colloids), liquids, and gases. Chromatographic samples generally receive some type of pre-treatment or conditioning prior to chromatography analysis. Samples can include a mixture of analytes and non-analytes. The term "analyte" is intended to refer to any sample component of interest that can be analyzed by chromatography, while the term "non-analyte" is intended to refer to any sample component for which chromatography analysis is not of interest in a given application. Non-limiting examples of non-analytes can include, to name a few, water, oils, solvents, and other media in which analytes may be found, as well as impurities and contaminants. It is noted that in some instances, the term "sample components" may be used interchangeably with the term "analytes" to refer to components of interest of a sample.

The present techniques can be used or implemented in various fields that may benefit from enhanced anomaly detection and diagnosis in chromatography applications. Non-limiting examples can include, to name a few, medical, pharmaceutical, food analysis, environmental, petrochemical, toxicology, forensic, and quality testing applications. In particular, the present techniques have potential use in GC-based breath gas analysis for the detection and diagnosis of diseases and disorders. Breath gas analysis is a non-invasive tool for medical research and diagnosis, which can be used to gain clinical information on the physiological state of an individual. Exhaled breath is mainly composed of nitrogen, oxygen, carbon dioxide, water vapor, and argon, which are generally non-analytes, along with trace amounts of volatile organic compounds (VOCs), among which some may be diagnostically useful analytes. Breath gas analysis involves the identification and quantification of analytes that provide biomarkers indicative of various pathologies and conditions. Non-limiting examples of such pathologies and conditions can include, to name a few, cancer, respiratory, pulmonary, kidney, and liver diseases, diabetes, alcohol intoxication, organ rejection, sleep apnea, and mental and physical stress.

Various implementations of the present techniques will now be described with reference to the figures. It is noted that the figures generally depict fluid flows with solid lines and communication links with dashed lines.

FIG. 1 is a schematic representation of a possible embodiment of a gas chromatography (GC) system 100 that can be used to implement the present techniques. The GC system 100 allows for the separation (or partial separation) of a vaporized or gaseous sample into its components, by passing a mobile phase carrying the gas sample through a stationary phase, and the subsequent detection and analysis of the separated components. In the illustrated embodiment, the gas sample is an exhaled breath sample, although various other types of samples, including gases, vaporized liquids, and vaporized solids, can be analyzed in other embodiments. It is also appreciated that although the illustrated embodiment is directed to a GC system, the present techniques may be implemented in any suitable chromatography system, including LC systems, such as high-performance liquid chromatography (HPLC) systems.

The GC system 100 of FIG. 1 generally includes a sample handling unit 102, a carrier gas unit 104, a chromatographic separation unit 106, a detection unit 108, and a control and processing unit 110. More detail regarding the structure and operation of these units and other possible components of the GC system 100 will be provided below. It is appreciated that FIG. 1 is a simplified schematic representation that illustrates a number of basic components of the GC system 100, such that additional features and components that may be useful or necessary for the practical operation of the GC system 100 may not be specifically depicted. Non-limiting examples of such additional features and components can include, to name a few, purge lines to remove dead volumes, pressure and flow regulators, restrictors, and other standard hardware and equipment. It is also appreciated that the theory, instrumentation, operation, and application of chromatography systems and methods are generally known in the art, and need not be described detail herein other than to facilitate an understanding of the present techniques.

The sample handling unit 102 includes the instrumentation of the GC system 100 that is configured for handling the sample to analyze, which can include steps such as collecting or receiving the sample; processing the sample to make it suitable for GC analysis; and dosing and injecting the processed sample as part of a mobile phase into the chromatographic separation unit 106. As can be appreciated, the sample handling unit 102 can include various hardware components, such as inlets, outlets, flow lines, containers, chambers, sample loops and traps, flow directing and regulating equipment (e.g., pumps and valves, flow metering equipment, filters), and the like, all of which are generally known in the art and need not be described in detail herein.

In FIG. 1, the sample handling unit 102 generally includes a sample collector 112, a sample conditioner 114, and a sample injector 116. It is appreciated that although the sample handling unit 102 in FIG. 1 is described as including modules performing specific functions (i.e., collection, conditioning, and injection), other embodiments may include modules that combine and add to functions of the modules of the sample handling unit 102 depicted in FIG. 1.

The sample collector 112 can include any device or combination of devices configured for collecting or sampling exhaled breath from a subject 118, which can involve exhalation through a face mask or into a bag.

The sample conditioner 114 can include any device or combination of devices configured for preparing, treating, or otherwise conditioning the sample into a gas sample suitable for injection as part of a mobile phase into the chromatographic separation unit 106. It is appreciated that the sample conditioner 114 can be configured to perform a variety of processing steps. Non-limiting examples of such steps can include, to name a few, steps of controlling the temperature, pressure, concentration, and/or flow of the sample, as well as various other pretreatment steps, such as sample accumulation, storage, filtering, division, purification, extraction, drying, vaporization, derivatization, enhancement, mixing, and any combination thereof.

Figure 8:
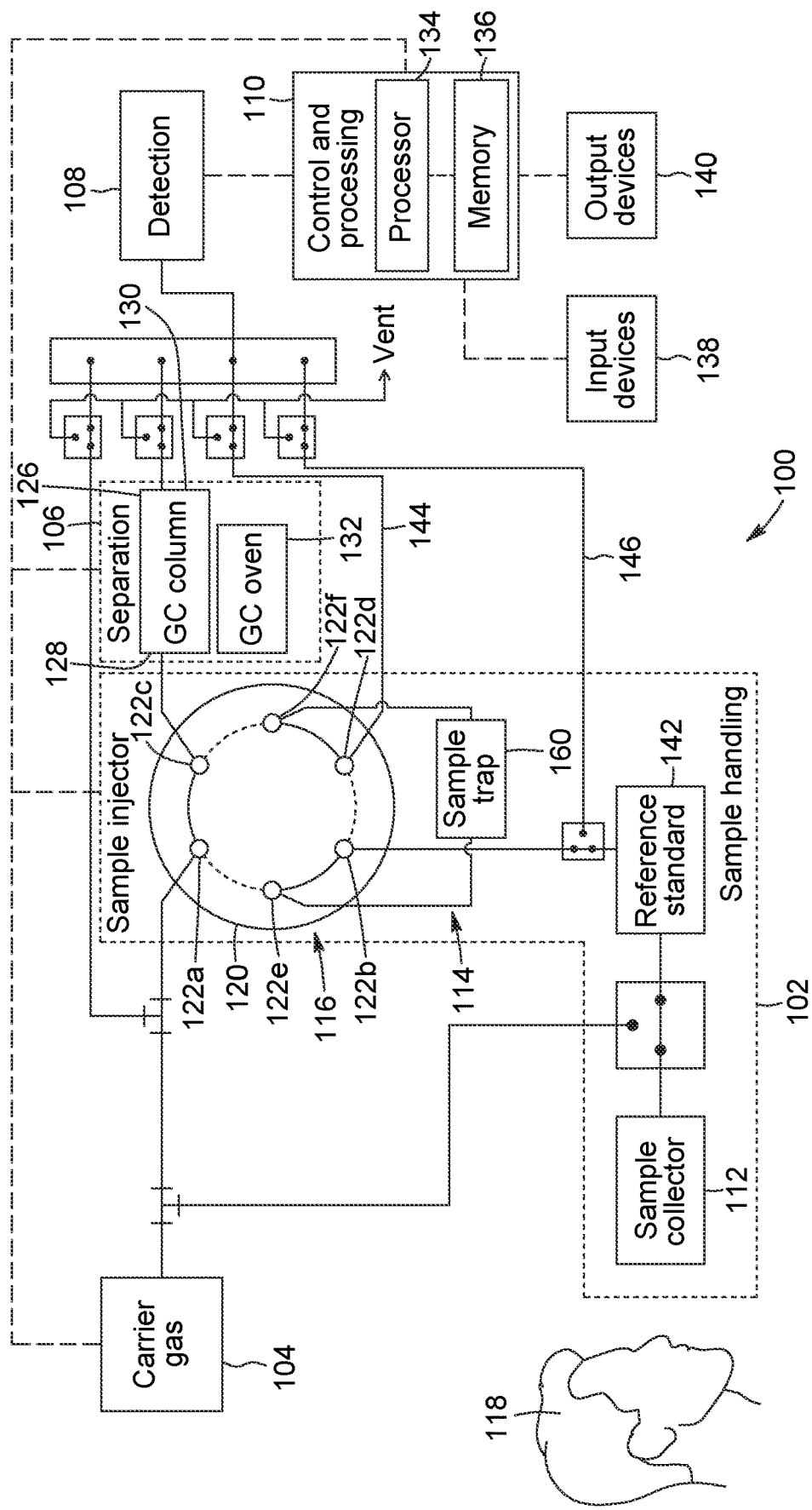
FIG. 8 is a schematic representation of another possible embodiment of a GC system.
Figure 9:
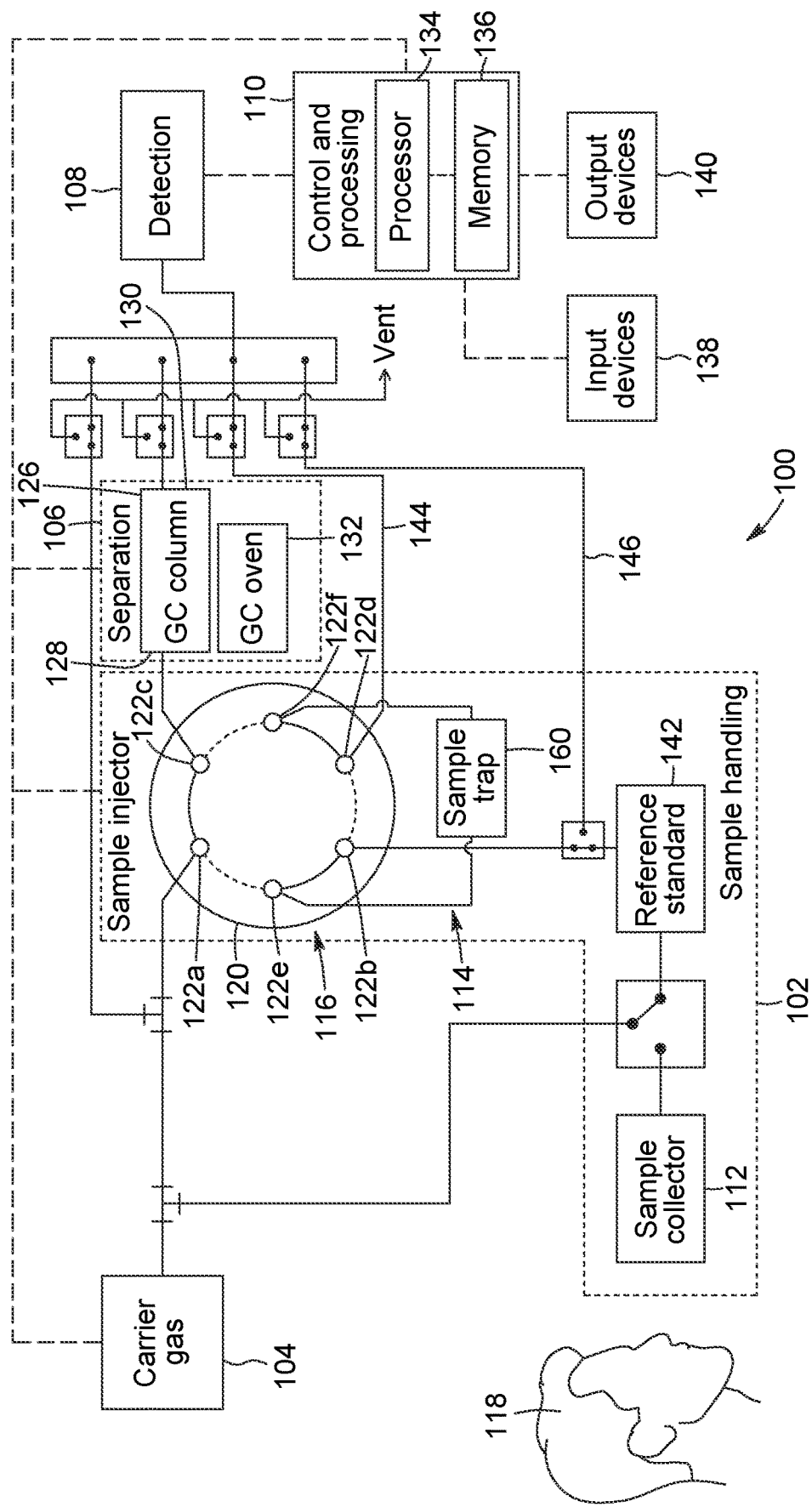
FIG. 9 is a schematic representation of another possible embodiment of a GC system.

The sample injector 116 can include any device or combination of devices configured for injecting the gas sample into the chromatographic separation unit 106. In FIG. 1, the gas sample is introduced into the carrier gas flow supplied by the carrier gas unit 104, and the resulting sample-carrier gas mixture is flown, as the mobile phase, into the chromatographic separation unit 106. The sample injector 116 may include a syringe, which can be manually operated or part of an autosampler, or other fluid delivery devices configured for injecting the gas sample into the stream of carrier gas supplied by the carrier gas unit 104. In FIG. 1, the sample injector 116 include a multiport switching valve 120, although other fluid directing devices for combining and directing fluid flows may be provided in other embodiments. In FIG. 1, the multiport switching valve 120 is a six-port switching valve having a first inlet port 122a connected to the carrier gas unit 104, a second inlet port 122b connected to the sample conditioner 114 (e.g., via a syringe), a first outlet port 122c connected to the chromatographic separation unit 106, a second outlet port 122d defining a sample vent, and two ports 122e, 122f defining a sample loop 124. In other embodiments, the sample loop 124 may be replaced by a sample trap configured for sample concentration, as illustrated in FIGS. 8 and 9. It is noted that in FIG. 1, the multiport switching valve 120 is depicted in a sample injection configuration, in which the connections between the inlet and outlet ports are depicted by solid lines. It is appreciated that the multiport switching valve 120 can be switched to a sample loading configuration, in which the connections between the inlet and outlet ports are depicted by dotted lines. The structure and operation of multiport switching valves used for sample injection in GC applications are known in the art and need not be described in detail herein. It is also appreciated that the present techniques can employ any suitable sample injection method, which can be performed on an automated, semi-automated, or manual basis.

The carrier gas unit 104 can include any device or combination of devices configured for supplying a flow of carrier gas for providing a suitable mobile phase for conveying the gas sample into and through the chromatographic separation unit 106. The carrier gas unit 104 can include a carrier gas source (e.g., a gas storage tank or cylinder), carrier gas supply lines (e.g., conduits, such as tubes or pipes) to convey the carrier gas between the carrier gas source and the chromatographic separation unit 106 via the sample handling unit 102, and flow regulators (e.g., pumps, valves, and restrictors) to control the carrier gas flow rate and pressure. The carrier gas is introduced with the gas sample upstream of the chromatographic separation unit 106, typically at or near the sample injector 116, for example, via a multiport switching valve 120, such as depicted in FIG. 1 (e.g., via the first inlet port 122a). The carrier gas can be any gas capable of providing a suitable mobile phase for carrying the gas sample, non-limiting examples of which can include, to name a few, helium, nitrogen, argon, air, oxygen, and hydrogen.

The chromatographic separation unit 106 can include a GC column 126 or another chromatographic device or combination of devices able to separate the gas sample into its constituents. Non-limiting examples of GC columns include packed columns and capillary columns. The GC column 126 has a column inlet 128 and a column outlet 130. The column inlet 128 is fluidly connected to the sample handling unit 102 and the carrier gas unit 104 via the sample injector 116 (e.g., via the first outlet port 122c of the multiport switching valve 120). The column outlet 130 is fluidly connected to the detection unit 108. The GC column 126 may be housed in or otherwise associated to a thermally controlled GC oven 132. The GC oven 132 can have any appropriate configuration for maintaining the GC column 126 at a selected temperature or for varying the temperature of the GC column 126 according to a selected temperature profile. The chromatographic separation unit 106 contains a stationary phase suitable for GC, which can include particles or films deposited on the inner surface of the GC column 126. The composition of the stationary phase may be selected so that different sample components in the gas sample exhibit different interaction strengths with the stationary phase, leading to different retention times. Thus, as the mobile phase flows through the GC column 126, the gas sample gradually separates into discrete sample components. The separated sample components eluting at the column outlet 130 are received and detected by the detection unit 108.

The detection unit 108 can include any appropriate detector or combination of detectors configured for providing qualitative and/or quantitative measurement of the separated sample components eluting from the chromatographic separation unit 106. Generally, the detection unit 108 is configured to respond to a property of the separated sample components, generate electrical detection signals based on the measured property, convert the generated electrical detection signals into digital detection signals, and supply the digital detection signals to the control and processing unit 110 for analysis, display, and/or storage. Various types of chromatography detectors exist and can be classified in different ways, including destructive or non-destructive, selective or universal, and concentration-sensitive or mass-sensitive detectors. Non-limiting examples of chromatography detectors include a flame ionization detectors (FID), a thermal conductivity detector (TCD), an electron capture detector (ECD), a flame thermionic detector (FTD), a flame photometric detectors (FPD), an atomic emission detector (AED), an optical emission spectroscopy (OES) detector, a nitrogen phosphorus detector (NPD), a mass spectrometer (MS), electrolytic conductivity detector (ELCD), a plasma emission detector (PED), an enhanced plasma discharge (Epd) detector, a UV detector, a fluorescence detector, and a photoionization detector (PID). In some embodiments, the detection unit 108 may include a combination of two or more different types of detectors. For example, in some embodiments, the detection unit 108 may be integrated into an analytical instrument, such as a mass spectrometer (MS) or an ion mobility spectrometer (IMS). The choice of a suitable detector can be made based on a number of factors, such as the type and number of analytes to be detected, the type of analytical information to be derived from the detected analytes, the desired or required accuracy and precision of the analysis, cost and space considerations, and the like.

The control and processing unit 110 is configured for controlling, monitoring, and/or coordinating the functions and operations of various components of the GC system 100, such as, for example, the sample handling unit 102, the carrier gas unit 104, the chromatographic separation unit 106, and the detection unit 108, as well as various temperature, pressure, and flow rate conditions. The control and processing unit 110 is also configured to analyze the detection signals received from the detection unit 108 to derive information about the presence and concentration of analytes in the gas sample under analysis. For example, the control and processing unit 110 can process the detection signals into a chromatogram, which is a graphical representation of the detector response plotted as a function of retention time. The chromatogram generally provides a spectrum of peaks representing the analytes present in the sample eluting from the chromatographic separation unit 106 and into the detection unit 108 at different retention times. The retention time of each peak can be used to identify the sample component, while the peak height or area can be used to the quantity of the sample component in the gas sample. Other peak parameters, such as peak shape and peak width, can also be considered in the analysis. It is appreciated that the principles underlying the processing of chromatographic data to derive analytical information about a test sample are generally known in the art, and need not be described in detail other than to facilitate an understanding of the techniques disclosed herein.

The control and processing unit 110 can be implemented in hardware, software, firmware, or any combination thereof, and be connected to various components of the GC system 100 via wired and/or wireless communication links to send and/or receive various types of signals, such as timing and control signals, measurement signals, and data signals. The control and processing unit 110 may be controlled by direct user input and/or by programmed instructions, and may include an operating system for controlling and managing various functions of the GC system 100. Depending on the application, the control and processing unit 110 may be fully or partly integrated with, or physically separate from, the other hardware components of the GC system 100. In FIG. 1, the control and processing unit 110 generally includes a processor 134 and a memory 136.

The processor 134 may be able to execute computer programs, also generally known as commands, instructions, functions, processes, software codes, executables, applications, and the like. It should be noted that although the processor 134 in FIG. 1 is depicted as a single entity for illustrative purposes, the term "processor" should not be construed as being limited to a single processor, and accordingly, any known processor architecture may be used. In some implementations, the processor 134 may include a plurality of processing units. Such processing units may be physically located within the same device, or the processor 134 may represent processing functionality of a plurality of devices operating in coordination. For example, the control and processing unit 110 may include a main processor configured to provide overall control and one or more secondary processors configured for dedicated control operations or signal processing functions. Depending on the application, the processor 134 may include or be part of a computer; a microprocessor; a microcontroller; a coprocessor; a central processing unit (CPU); an image signal processor (ISP); a digital signal processor (DSP) running on a system on a chip (SoC); a single-board computer (SBC); a dedicated graphics processing unit (GPU); a special-purpose programmable logic device embodied in hardware device, for example, a field-programmable gate array (FPGA) or an application-specific integrated circuit (ASIC); a digital processor; an analog processor; a digital circuit designed to process information; an analog circuit designed to process information; a state machine; and/or other mechanisms configured to electronically process information and to operate collectively as a processor.

The memory 136, which can also be referred to as a computer readable storage medium, is capable of storing computer programs and other data to be retrieved by the processor 134. The terms "computer readable storage medium" and "computer readable memory" are intended to refer herein to a non-transitory and tangible computer product that can store and communicate executable instructions for the implementation of various steps of the methods disclosed herein. The computer readable memory can be any computer data storage device or assembly of such devices, including random-access memories (RAMs); dynamic RAMs; read-only memories (ROMs); magnetic storage devices, such as hard disk drives, solid state drives, floppy disks, and magnetic tapes; optical storage devices, such as compact discs (e.g., CDs and CDROMs), digital video discs (DVDs), and Blu-Ray™ discs; flash drive memories; and/or other non-transitory memory technologies. A plurality of such storage devices may be provided, as can be appreciated by those skilled in the art. The computer readable memory may be associated with, coupled to, or included in a computer or processor configured to execute instructions contained in a computer program stored in the computer readable memory and relating to various functions associated with the computer or processor.

The GC system 100 may also include one or more user interface devices operatively connected to the control and processing unit 110 to allow the input of commands and queries to the GC system 100, as well as present the outcomes of the commands and queries. The user interface devices can include input devices 138 (e.g., a touch screen, a keypad, a keyboard, a mouse, a switch, and the like) and output devices 140 (e.g., a display screen, a printer, visual and audible indicators and alerts, and the like).

As noted above, the present description relates to techniques for monitoring, detecting, and diagnosing anomalies in chromatography applications. As will now be described, the present techniques involve the use of reference standards.

The term "reference standard" is intended to refer to a substance whose amount or concentration is known and whose response is compared to that of a sample being analyzed for analyte identification and/or quantification. Reference standards can be used as internal standards or external standards.

For analyte identification, a reference standard can be used to calculate the relative retention time (RRT) of a target analyte, which can involve computing the ratio of the retention time of the analyte to the retention time of the standard. The use of RRTs can allow for the compensation of retention time drifts. Retention time drifts can arise from various sources of variation, which can be related to the instrumentation, the materials, environmental and processing conditions, and operator errors.

For analyte quantification, a reference standard can be used to provide a reference response factor. The term "response factor" is intended to refer herein to a ratio between a detector response or signal produced by a compound and the amount or concentration of the compound which produces the detector response or signal. In a chromatogram, a reference response factor can be calculated as the ratio of the peak area of the standard to the amount or concentration of the standard. The response factor of the reference standard can be used to calculate the relative response factor (RRF) of a target analyte, which can involve computing the ratio of the response factor of the analyte to the response factor of the standard. It is noted that the terms "response factor" and "relative response factor" are intended to refer not only to individual factors, but also, notably in the case of a nonlinear detector response, to a "response function" and a "relative response function", defined to cover a range of amounts or concentrations. The use of RRFs can allow for the compensation of variations in sample preparation, dosage, and injection, chromatographic separation, and detection between different analyses. As for RRT drifts, such variations can arise from a number of sources (e.g., instrumentation, environment, process conditions, materials, human factors, and the like).

An internal standard is a non-analyte substance that is added in a known amount or concentration to a sample containing analytes and that is used to measure the relative responses of the analytes. The internal standard is present in the various samples that are analyzed, including both calibration samples and test samples. The method of internal standards aims to improve the precision of quantitative analysis. The purpose of an internal standard is to behave similarly to the analytes, such that any factor affecting the analytes should ideally also affect the internal standard in the same or substantially the same way. Thus, the ratio of the analyte signals to the internal standard signal should exhibit less variability than the analyte signals alone. However, the internal standard should be sufficiently different from any of the analytes to produce a chromatographically resolved peak. Furthermore, internal standards should be available in pure form, should be stable, should not be found in the sample, should be stable and inert to the sample, and should not be interfering with analyte identification and quantification. The method of internal standards can include an initial calibration procedure using either a single-point or a multi-point calibration approach.

In single-point calibration, a single calibration sample is used, which contains known amounts of analytes and a predetermined amount of the internal standard. The response factor $RF_{IS}$ of the internal standard, the response factor $RF_n$ of the $n^{th}$ analyte, and the relative response factor $RRF_{n-IS}$ of the $n^{th}$ analyte relative to the internal standard can be calculated as follows:

$$RF_{IS} = \frac{A_{IS}}{C_{IS}}, \tag{1}$$

$$RF_n = \frac{A_n}{C_n}, \tag{2}$$

$$RRF_{n-IS} = \frac{RF_n}{RF_{IS}} = \frac{A_n/C_n}{A_{IS}/C_{IS}} = \frac{A_n/A_{IS}}{C_n/C_{IS}}, \tag{3}$$

where $A_{IS}$ and $C_{IS}$ are the measured peak area and the known amount of the internal standard, respectively, and $A_n$ and $C_n$ are the measured peak area and the known amount of the $n^{th}$ analyte, respectively. The unknown amount of the $n^{th}$ analyte in a test sample containing the predetermined amount $C_{IS}$ of internal standard can then be obtained from Equation (3), as follows:

$$C_n = \left(\frac{A_n}{A_{IS}}\right)\left(\frac{1}{RRF_{n-IS}}\right)C_{IS}, \tag{4}$$

where the peaks areas $A_n$ and $A_{IS}$ are determined from the measured chromatogram, the relative response factor $RRF_{n-IS}$ is known from the calibration, and $C_{IS}$ is assumed known.

In multi-point calibration, multiple calibration samples are used. Each calibration sample contains known amounts of analytes and a predetermined amount of the internal standard. The known amounts of analytes vary among the different calibration samples, so as to cover the range of expected amounts in test samples. The relative response factor $RRF_{n-IS}$ of the $n^{th}$ analyte are obtained for each calibration sample, using Equations (1) to (3). Then, an RRF calibration curve for the $n^{th}$ analyte can be constructed. The calibration curve relates the ratio $A_n/A_{IS}$ to the ratio $C_n/C_{IS}$, the relationship between the two ratios representing the variation of the relative response factor $RRF_{n-IS}$ as a function of the amount of the $n^{th}$ analyte. The unknown amount of the $n^{th}$ analyte in a test sample containing the predetermined amount $C_{IS}$ of internal standard can then be obtained by performing the following steps: determining the ratio $A_n/A_{IS}$ from the measured chromatogram; determining, from the RRF calibration curve, the ratio $C_n/C_{IS}$ that corresponds to the measured ratio $A_n/A_{IS}$, either directly or by interpolation; and multiplying the determined ratio $C_n/C_{IS}$ by the known $C_{is}$ to obtain $C_n$.

It is appreciated that although the addition of a single internal standard was considered above, the use of multiple internal standards can be advantageous or even required in some embodiments, notably in the case of samples containing a large number of target analytes and/or target analytes that elute over a long period of time. For example, in the latter case, the multiple internal standards may be chosen so that their retention times cover the range of expected retention times of the analytes. Furthermore, in some implementations, as the ratio between the retention times of pairs of peaks can convey information about column performance and operating conditions, using at least two internal standards can allow such retention time ratios to be computed and used to assess column and overall system performance.

In external standard calibration, analyte quantification involves the comparison between the chromatogram of a test sample containing unknown amounts of target analytes and the chromatogram(s) of a single or multiple calibration samples containing known amounts of the target analytes. External standards may be useful when suitable internal standards cannot be found, for example, due to insufficient chromatographic separation with the target analytes. In single-point calibration, the calibrated response factor $RF_n$ of the $n^{th}$ analyte in the calibration sample is determined using $RF_n = A_n/C_n$, where $A_n$ and $C_n$ are the measured peak area and the known amount of the $n^{th}$ analyte, respectively. The unknown amount of the $n^{th}$ analyte in a test sample can then be obtained by dividing the measured peak area $A_n$ of the $n^{th}$ analyte in the test sample by the calibrated response factor $RF_n$. In multi-point calibration, the peak area $A_n$ of the $n^{th}$ analyte is recorded for each calibration sample, where the known amounts of the $n^{th}$ analyte vary among the different calibration samples, so as to cover the range of expected amounts in test samples. Then, an RF calibration curve for the $n^{th}$ analyte can be constructed, which represents the variation of the response factor $RF_n$ of the $n^{th}$ analyte as a function of its amount. The unknown amount of the $n^{th}$ analyte in a test sample can then be determined by measuring its peak area $A_n$ and fitting it into the calibration curve.

It is appreciated that the principles underlying the theory and use of internal and external standards for analyte identification and quantification in chromatography applications are generally known in the art, and need not be described detail herein other than to facilitate an understanding of the present techniques.

Returning to FIG. 1, the sample handling unit 102 further includes a reference standard module 142. The reference standard module 142 can include any device or combination of devices configured for adding a reference standard to the sample under analysis. Non-limiting examples of such devices include permeation-tube-based system and calibration bottles containing dilute mixtures. In the illustrated embodiment, the reference standard added by the reference standard module 142 is an internal standard, although the use of external standards is not a priori excluded in other embodiments. As noted, the amount of internal standard added to the sample is known and well-controlled, and is generally the same for every sample, that is, both unknown and calibration samples.

The choice of a suitable internal standard, and the number of internal standards used, can be made based on a number of factors, such as the type and number of analytes to be detected, the type of analytical information to be derived from the detected analytes, sensitivity requirements, cost and material availability considerations, and the like. As noted above, a suitable internal standard should be chemically similar to the sample in order to exhibit a similar behavior during analysis; it should give a well-resolved peak but elute close to the target analytes; and it should not be interfering with analyte identification and quantification. For example, in the case of an exhaled breath sample, non-limiting examples of substances that can be used as internal standards may include substances with the same or a similar chemical functional group, the same or a similar molecular weight, the same or a similar polarity, the same or a similar response behavior in the detector, the same or similar chromatographic separation characteristics, and the like.

It is appreciated that various methods exist both for preparing internal standards and for introducing internal standards into a sample, and that the present techniques can employ any suitable internal standard preparation and introduction method, which can be performed on an automated, semi-automated, or manual basis. For example, the internal standard may be added to the sample via a dedicated gas circuit. In such a case, the internal standard may be supplied in a gas matrix, or using a permeation tube, as in FIG. 1. When the internal standard is contained in a gas matrix, the gas matrix may be the same as the sample gas matrix (e.g., air if the sample is exhaled breath) or the same as the carrier gas.

It is customary to add the internal standard to the sample as upstream as possible in the chromatography process. In this way, the use of the internal standard can compensate for variations in the operation of the GC system 100 occurring at various process stages and involving different system components, including during the step of sample preparation, the step of sample injection, the step of chromatographic separation, and the step of analyte detection. As noted above, variations in the operation of the GC system 100 can have a number of causes, including instrumentation-related causes (e.g., malfunction, wear, aging, damage, degradation, failure, pollution, inherent variability of hardware equipment), environmental causes (e.g., variations in ambient conditions, such as pressure, temperature, and humidity), and operator-related causes (e.g., human errors). In the illustrated embodiment, the internal standard is added to the sample at a point located between the sample collector 112 and the sample conditioner 114, although the internal standard could be added to the sample at different points of the GC system 100 in other embodiments, for example, at the sample collection point.

In some embodiments, the reference standard may be used in a double-injection approach. In such a case, the process can include a first injection step with the test sample to be analyzed, and a second injection step with a standard sample containing the reference standard. Depending on the application, the injection of the test sample may be performed either before or after the injection of the standard sample. In some embodiments, the two injection steps can be performed with little to no delay between them, in order reduce possible sources of variation in chromatographic separation and detector response, as well as to not unduly lengthen the measurement process. In such a case, the response of the test sample and the response of the standard sample may be measured sufficiently close in time and under sufficiently similar conditions to be represented on the same chromatogram.

It is appreciated that the use of a standard sample which is distinct from the test sample entails not only distinct injection steps, but also distinct preparation steps. Thus, in such a case, the reference standard may not be used to compensate for variations occurring during sample preparation and injection, such as instrumentation variability and operator errors, as well as sample loss, contamination, or damage. It is appreciated that depending on the application, the standard sample may be prepared and injected into the chromatographic separation unit 106 by passing through the sample conditioner 114 and the sample injector 116 along the same path as the test sample, as in FIG. 1, or along a partially or completely different path. Furthermore, the delay, if any, between the two injection steps can be adjusted or controlled to avoid co-elution between the reference standard contained in the standard sample and any of the analytes contained in the test sample, thus ensuring that the reference standard produces a chromatographically resolved response. It is appreciated that in such a double-injection approach, the reference standard used need not be absent from the test sample. That is, in some embodiments, the reference standard may have the same composition as one of target analytes found in the test sample. For example, in breath analysis applications, the reference standard can include benzene, styrene, toluene, hydrogen sulfide, or a combination thereof, which can be found in typical exhaled breath samples. In such a case, such a reference standard can be referred to as a separately injected internal standard. In any event, embodiments implementing a double-injection approach can use internal and external standard calibration methods, such as described above, for analyte calibration purposes and real-time compensation of RRT and RRF drifts.

In some embodiments, it may not be desirable or required that the reference standard compensate for RRT drifts. In such a case, the standard sample and the test sample may be detected by the same detector of the detection unit, but be separated along different GC columns in the chromatographic separation unit 106. Furthermore, depending on the application, the standard sample and the test sample may pass through the sample conditioner and the sample injector along the same path, a partially different path, or a completely different path.

Internal standards can be used to improve the precision and accuracy of quantitative analysis by compensating for variations in the response of the chromatographic system between analyses, based on the principle that variations affecting the analyte responses will affect the internal standard response in the same way. As noted above, such variations can occur at any point during sample preparation, dosage and injection, chromatographic separation, and detection. Non-limiting examples of sources of variation can include, to name a few, sample losses during sample preparation, variations in sample injection volume, variations in process conditions (e.g., pressure, temperature, humidity), aging or pollution of the chromatographic column, and detector problems due to noise, drift, or sensitivity.

Furthermore, since an internal standard is generally introduced in the same amount in all of the samples, including all test samples and calibration samples, it can be envisioned to monitor the response of the internal standard over time in order to detect possible anomalies in the operation of the chromatography system. For example, in some embodiments, the present techniques can monitor the response of an internal standard in all test samples for variations with respect to an expected response. As can be appreciated, the expected internal standard response, against which a current internal standard response is evaluated, may be established by a prior calibration procedure or in any other suitable manner. Depending on the application, the internal standard response can be monitored in terms of various peak parameters, such as the peak area, peak height, peak shape, peak width, peak signal-to-noise ratio (SNR), and the like, or system parameters, such as baseline noise and signal drift. It is appreciated that monitoring the response of an internal standard in terms of its response factor may not be appropriate in some embodiments, since the actual amount or concentration of the internal standard added to any test sample is only assumed to be known, but cannot generally be measured directly.

It is appreciated that beyond a certain threshold, variations in the internal standard response may become undesirable or unacceptable. This is because such variations may lead to reduced sensitivity and inaccurate analysis and may be indicative of operation and/or performance issues with the chromatography system. It is therefore relevant to monitor, preferably automatically and in real-time, the internal standard response for possible anomalies during chromatography analysis of test samples. However, because internal standards are generally added to the sample at the beginning of chromatography analysis, prior to sample preparation and injection, determining the cause of a detected anomaly in the internal standard response may not be straightforward. Indeed, since an internal standard goes, along with the test sample, through the steps of sample preparation, sample injection, chromatographic separation, and detection, an anomaly found in the internal standard response recorded on the chromatogram could be attributed to any, some, or all of these steps. Thus, making a diagnosis about the cause of an observed anomaly, for example, in view of performing a corrective action, can be challenging and tedious.

Returning to FIG. 1, in some implementations, the present techniques aim to address these limitations, by determining expected standard responses associated with different components of the GC system 100, for example, the sample handling unit 102, the chromatographic separation unit 106, and the detection unit 108. As for the expected standard response associated with the overall GC system 100, the expected standard responses associated with specific units of the GC system 100 can also be determined by precalibration procedures. For simplicity, the expected standard response associated with the overall GC system 100 will be referred to hereinbelow as the "expected overall standard response", while the expected standard responses associated with specific units of the GC system 100 will be referred to hereinbelow as the "expected specific standard responses".

In some embodiments, three expected specific standard responses can be defined: a first expected specific standard response associated with the sample handling unit 102, designated herein as $R_{S\text{-}SAMPLE}$; a second expected specific standard response associated with the chromatographic separation unit 106, designated herein as $R_{S\text{-}SEP}$; and a third expected specific standard response associated with the detection unit 108, designated herein as $R_{S\text{-}DET}$. The expected overall standard response will be designated as $R_O$. It is to be noted that, as for the overall response $R_O$, the specific responses $R_{S\text{-}SAMPLE}$, $R_{S\text{-}SEP}$, and $R_{S\text{-}DET}$ to be monitored can correspond to various peak parameters, or a combination of such peak parameters, that can be observed on a chromatogram, such as peak area, peak height, peak shape, peak width, peak signal-to-noise ratio (SNR), and the like. In some embodiments, the determination of the expected standard responses $R_O$, $R_{S\text{-}SAMPLE}$, $R_{S\text{-}SEP}$, and $R_{S\text{-}DET}$ from calibration measurements can be made fully automatically, for example, with the processor 134 alone, without operator input. However, in other embodiments, the determination can be made partly automatically, for example, with the processor 134 and some operator input.

Referring to FIGS. 2 to 5, the GC system 100 of FIG. 1 can be configured to allow for the overall and specific standards responses to be determined (e.g., for calibration purposes, to establish expected values of the overall and specific standards responses) and monitored (e.g., for anomaly detection purposes, to compare current values of the overall and specific standards responses against their expected values).

Figure 2:
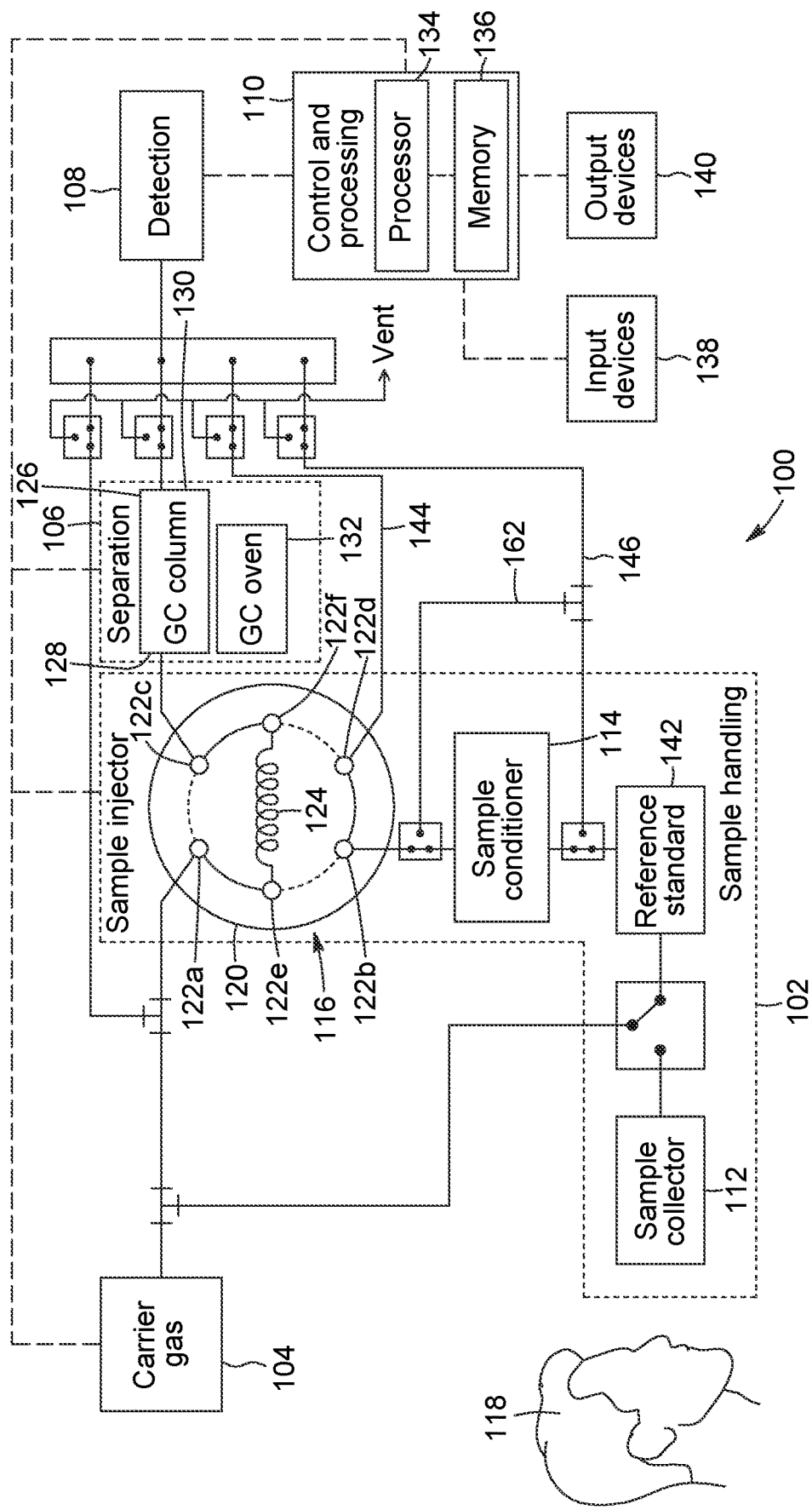
FIG. 2 is a schematic representation of the GC system of FIG. 1, depicted in another operation configuration.

Referring to FIG. 2, the expected overall standard response $R_O$ can be determined by a precalibration procedure. The procedure can involve performing a chromatography analysis of a first reference standard sample to obtain an overall reference chromatogram. The first reference standard sample includes the reference standard, in an amount that corresponds to the amount of reference standard added to the test samples in which the reference standard response will be monitored for variations from the expected overall standard response determined by the precalibration procedure.

During the chromatography analysis, the reference standard is supplied from the reference standard module 142 to the detection unit 108 by being flown successively through the sample conditioner 114 and the sample injector 116 of the sample handling unit 102, and the GC column 126 of the chromatographic separation unit 106. The expected overall standard response $R_O$ can be obtained by analyzing (e.g., using the processor 134, with or without operator input) peak information associated with the reference standard in the overall reference chromatogram generated by the control and processing unit 110 from the detection signal measured by the detection unit 108. As noted above, various peak parameters can be used to define the expected overall standard response $R_O$. For example, in some embodiments, the expected overall standard response $R_O$ is defined by a peak area. The expected overall standard response $R_O$ thus determined can be stored in the memory 136 for later use during the steps of anomaly monitoring and detection.

Figure 3:
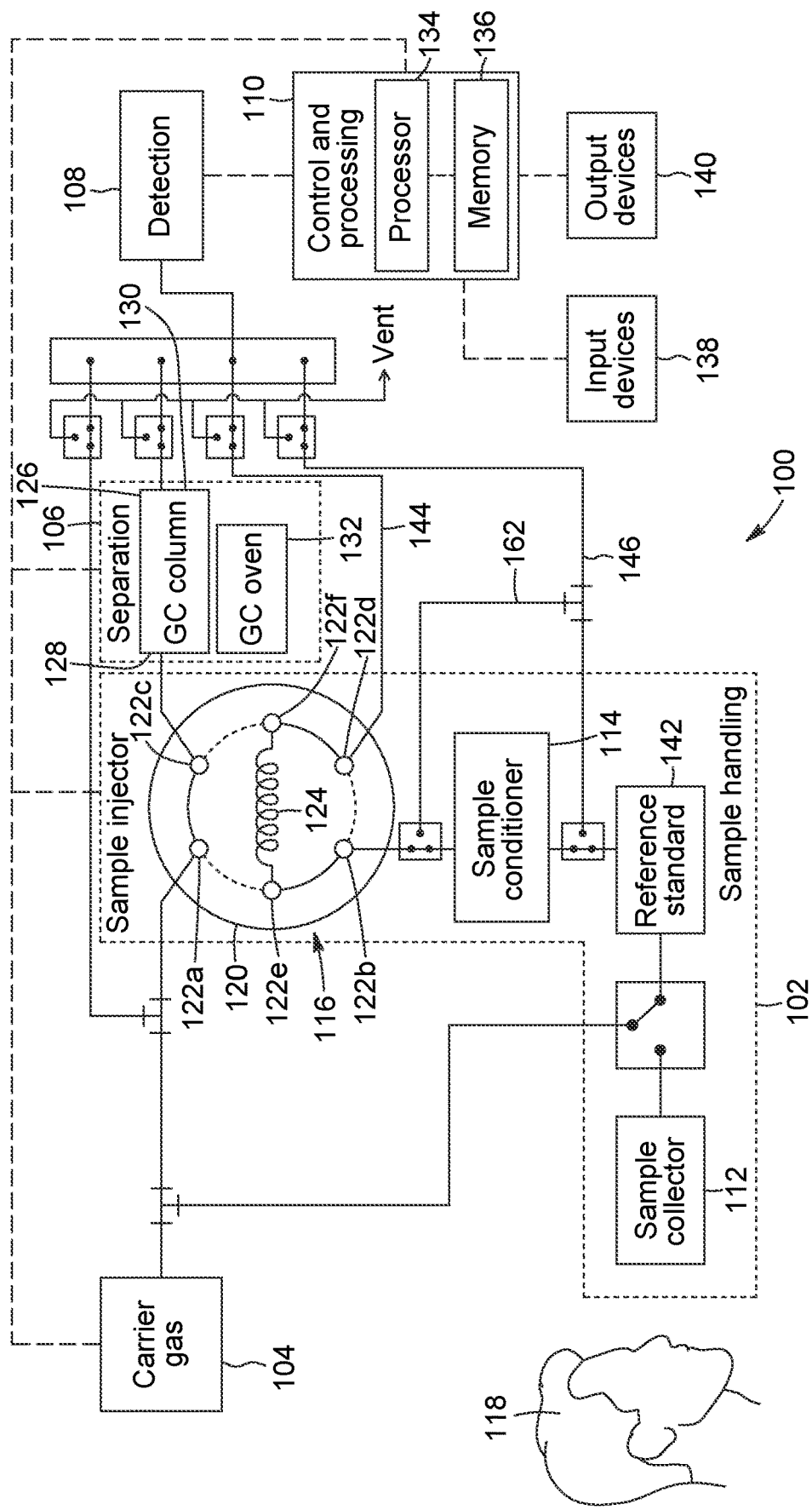
FIG. 3 is a schematic representation of the GC system of FIG. 1, depicted in another operation configuration.

Referring to FIG. 3, the GC system 100 is depicted in a configuration for determining the expected specific standard response $R_{S\text{-}SAMPLE}$ associated with the sample handling unit 102. The procedure can involve passing a second reference standard sample containing the reference standard through the sample conditioner 114 and the sample injector 116 under predetermined conditions and for a predetermined period of time; and subsequently releasing the second reference standard sample from the sample injector 116 into a flow path 144 fluidly connected to the detection unit 108 (or another detection unit, as the case may be). For example, the second reference standard sample can be concentrated by a sorbent provided inside the sample loop 124 of the sample injector 116, under predetermined conditions and for a predetermined period of time, and then released from the sample loop 124 and into the detection unit 108 via the sample vent 122d and the flow path 144 after the predetermined period of time has elapsed. The detection unit 108 is configured to detect the second reference standard sample exiting from the sample handling unit 102. The expected specific standard response $R_{S\text{-}SAMPLE}$ can be obtained (e.g., using the processor 134, with or without operator input) from the signal from the second reference standard sample detected by the detection unit 108. For example, the detected signal can include a peak representing the reference standard contained in the second reference standard sample, and the expected specific standard response $R_{S\text{-}SAMPLE}$ can be defined in accordance with a parameter of this peak, for example, a peak area. The expected specific standard response $R_{S\text{-}SAMPLE}$ can be stored in the memory 136 for later use during the steps of anomaly monitoring and detection. It is appreciated that because the second reference standard sample is detected without having passed through the chromatographic separation unit 106, the expected specific standard response $R_{S\text{-}SAMPLE}$ can allow for the performance of the sample handling unit 102 to be characterized (e.g., in terms of variability in injected sample volume during sample injection and/or in variability in sample losses during sample preparation) independently of any potential source of variation associated with the chromatographic separation unit 106.

Figure 4:
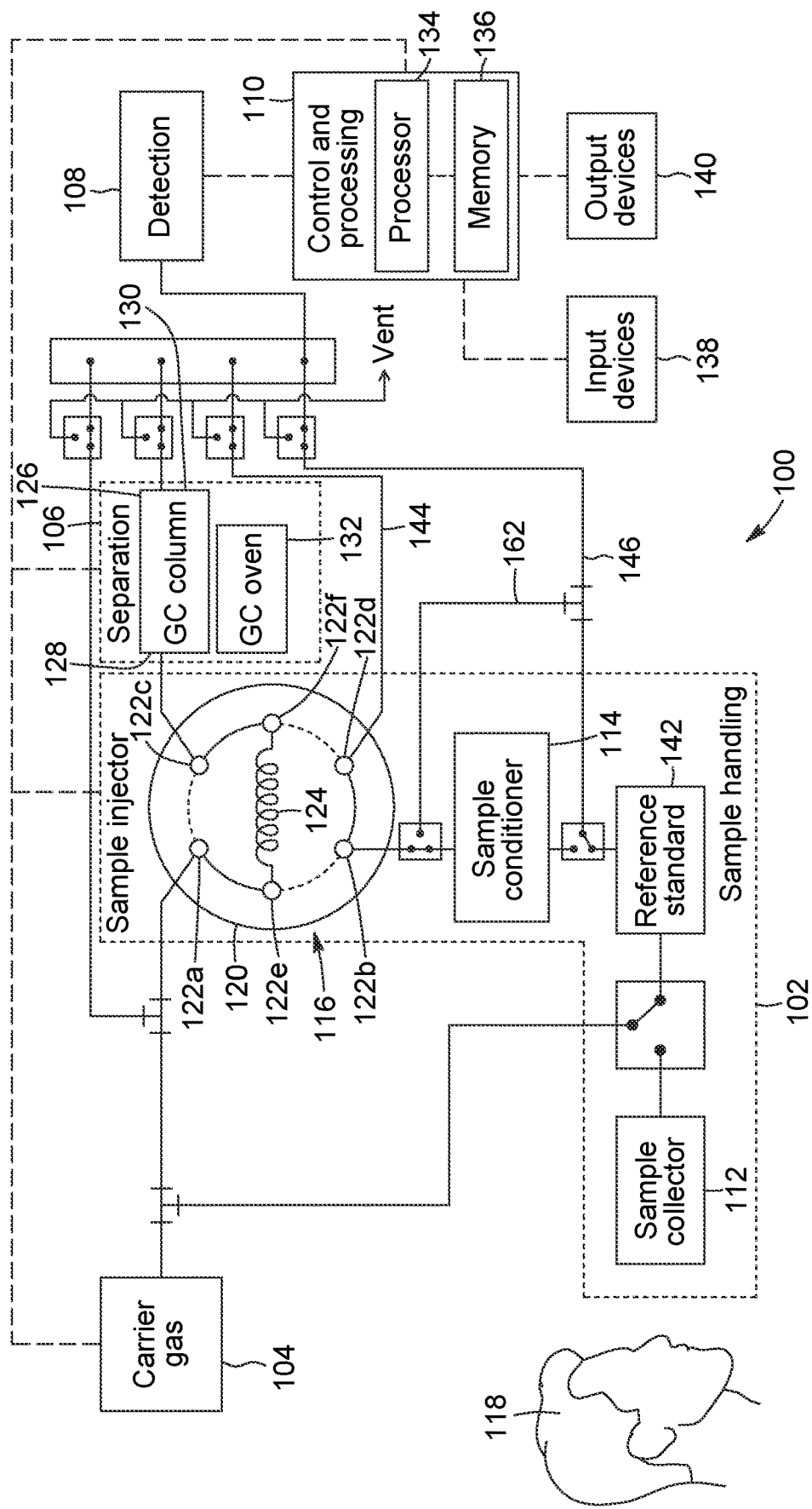
FIG. 4 is a schematic representation of the GC system of FIG. 1, depicted in another operation configuration.

Referring to FIG. 4, the GC system 100 is depicted in a configuration for determining the expected specific standard response $R_{S\text{-}DET}$ associated with the detection unit 108. The procedure can involve using the detection unit 108 to measure the response of a third reference standard sample containing a known amount or concentration of the reference standard. In FIG. 4, the third reference standard sample is supplied from the reference standard module 142 to the detection unit 108 via a suitable flow path 146. The expected specific standard response $R_{S\text{-}DET}$ can be obtained (e.g., using the processor 134, with or without operator input) from the signal from the third reference standard sample detected by the detection unit 108. For example, the detected signal can include a peak representing the reference standard contained in the third reference standard sample, and the expected specific standard response $R_{S\text{-}DET}$ can be defined in accordance with a parameter of this peak, for example, a peak area. The expected specific standard response $R_{S\text{-}DET}$ can be stored in the memory 136 for later use during the steps of anomaly monitoring and detection. It is appreciated that because the third reference standard sample is detected without having passed through the sample conditioner 114, the sample injector 116, and the chromatographic separation unit 106, the expected specific standard response $R_{S\text{-}DET}$ can allow for the performance of the detection unit 108 to be characterized (e.g., in terms of parameters such as noise, drift, and sensitivity) independently of any potential source of variation associated with the sample conditioner 114, the sample injector 116, or the chromatographic separation unit 106. In some embodiments, the expected specific standard response $R_{S\text{-}DET}$ determined in this manner can be used to determine or adjust the expected specific standard response $R_{S\text{-}SAMPLE}$, for example, by removing from $R_{S\text{-}SAMPLE}$ features that are related to the detection of the second reference standard sample by the detection unit 108.

The expected specific standard response $R_{S\text{-}SEP}$ associated with the chromatographic separation unit 106 can be determined in different ways. In some embodiments, the expected specific standard response $R_{S\text{-}SEP}$ can be related to an expected peak shape associated with the chromatographic separation unit 106. For example, the expected specific standard response $R_{S\text{-}SEP}$ can be defined from a peak shape analysis (e.g., using the processor 134, with or without operator input) of the shape of the peak used to determine the overall standard response $R_O$, as described above with respect to FIG. 2. Depending on the application, the shape of a chromatographic peak can be characterized by a number of parameters, which can be related to its width, its symmetry or asymmetry, its Gaussian or non-Gaussian character, its degree of tailing, fronting, or splitting, and the like. It is appreciated that the determination of the expected specific standard response $R_{S\text{-}SEP}$ based on peak shape may be advantageous in chromatography systems where peak shape is affected primarily by factors related to the performance of the chromatographic separation unit 106. Non-limiting examples of such factors can include, to name a few, column aging, column pollution, variations in packing density over time, stationary phase degradation, temperature, flow, and any combination thereof.

In another embodiment, the expected specific standard response $R_{S\text{-}SEP}$ can be determined from the expected overall standard response $R_O$ and the expected specific standard response $R_{S\text{-}SAMPLE}$ associated with the sample handling unit 102. This approach is based on the principle that the method of determining $R_O$ and the method of determining $R_{S\text{-}SAMPLE}$ differ from each other mainly in that the latter does not involve passing the reference standard sample through the chromatographic separation unit 106. Thus, the determination of the expected specific standard response $R_{S\text{-}SEP}$ associated with the chromatographic separation unit 106 can be made based on a subtraction of the expected specific standard response $R_{S\text{-}SEP}$ from the expected overall standard response $R_O$, or another suitable operation in which the expected specific standard response $R_{S\text{-}SEP}$ is used to remove features from the expected overall standard response $R_O$ that are not related to the passage of the first reference standard sample through the chromatographic separation unit 106. The expected specific standard response $R_{S\text{-}SEP}$ can be stored in the memory 136 for later use during the steps of anomaly monitoring and detection.

Figure 5:
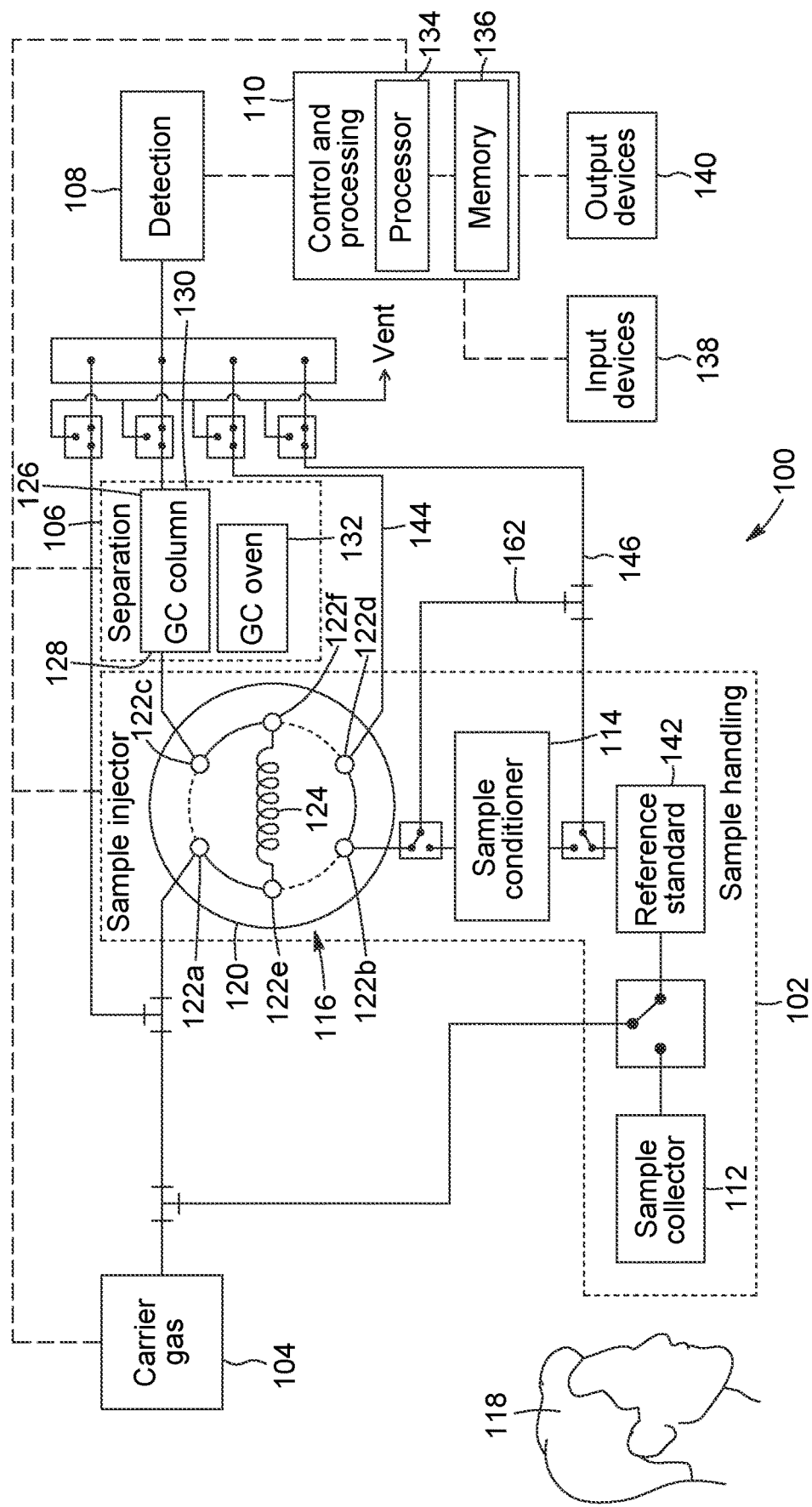
FIG. 5 is a schematic representation of the GC system of FIG. 1, depicted in another operation configuration.

Referring to FIG. 5, the GC system 100 is depicted in a configuration for determining the expected specific standard response $R_{S\text{-}SEP}$ associated with the chromatographic separation unit 106. The procedure can involve passing a fourth reference standard sample containing the reference standard from the reference standard module 142 to the sample injector 116 via a flow path 162 that bypasses the sample conditioner 114; and subsequently flowing the fourth reference standard sample through the GC column 126 of the chromatographic separation unit 106 and into the detection unit 108. The expected specific standard response $R_{S-SEP}$ can be obtained by analyzing (e.g., using the processor 134, with or without operator input) the peak associated with the reference standard in the signal from the fourth reference standard sample detected by the detection unit 108. For example, the detected signal can include a peak representing the reference standard contained in the fourth reference standard sample, and the expected specific standard response $R_{S-SEP}$ can be defined in accordance with a parameter of this peak, for example, a peak area. The expected specific standard response $R_{S-SEP}$ can be stored in the memory 136 for later use during the steps of anomaly monitoring and detection.

Once the expected standard responses $R_O$, $R_{S-SAMPLE}$, $R_{S-SEP}$, and $R_{S-DET}$ have been determined by calibration, such as described above, the method for anomaly detection and diagnosis can involve a step of using a chromatography system to perform a chromatography analysis of a test sample to obtain a chromatogram of the test sample. In the case of an exhaled breath sample, the chromatography analysis can be performed with the GC system 100 illustrated in FIG. 1. The test sample to be analyzed contains target analytes and a known amount or concentration of a reference standard (e.g., an internal standard). The reference standard generally has the same composition and amount or concentration as the reference standard used to the expected overall standard responses $R_O$. The chromatogram of the test sample provides a spectrum of peaks plotted as a function of retention time and including peaks associated with the target analytes and a peak associated with the reference standard. The method can include a step of analyte identification and quantification by comparing the RRTs and the RRFs of the analyte peaks with those obtained from calibration samples acquired under the same operating conditions used for the samples.

The method can also include an anomaly detection operation, which can involve a step of analyzing the chromatogram of the test sample to determine peak information corresponding to the reference standard in the chromatogram of the test sample, and a step of determining whether the peak information conforms with the expected overall standard response $R_O$. In some embodiments, determining whether the peak information conforms with the expected overall standard response $R_o$ can include determining, from the peak information, a current overall standard response $R_{O*}$ of the chromatography system associated with the reference standard, and assessing whether the current overall standard response $R_{O*}$ deviates from the expected overall standard response $R_O$ stored in memory by more than a predetermined threshold.

In some embodiments, the analyzing and assessing steps and the step of analyte identification and quantification may be performed concurrently or consecutively with little to no delay between them, so to lessen the impact of performing the anomaly detection operation on the overall duration of the chromatography analysis. If the deviation between the current overall standard response $R_{O*}$ and the expected overall standard response $R_O$ is less than or equal to the predetermined threshold, the method can determine that there is no anomaly in the operation of the chromatography system. However, if the deviation between the current overall standard response $R_{O*}$ and the expected overall standard response $R_o$ exceeds the predetermined threshold, the method can determine that there is an anomaly in the operation of the chromatography system.

Upon detection of an anomaly, the method can include a step of performing a diagnosis operation of the detected anomaly to determine its cause. The diagnosis operation can involve determining the cause of the anomaly as relating to at least one of the operation of the sample handling unit, the operation of the chromatographic separation unit, and the operation of the detection unit. For example, the anomaly diagnosis operation can include steps of determining a first, second, and third current specific standard responses $R_{S-SAMPLE*}$, $R_{S-SEP*}$, and $R_{S-DET*}$, such as described above with respect to FIGS. 2 to 5, and assessing, by performing a comparison operation, whether each one of the first, second, and third current specific standard responses $R_{S-SAMPLE*}$, $R_{S-SEP*}$, and $R_{S-DET*}$ thus determined deviates from the respective one of the first, second, and third expected specific standard responses $R_{S-SAMPLE}$, $R_{S-SEP}$, and $R_{S-DET}$ by more than a respective predetermined threshold. If the deviation, if any, between $R_{S-SAMPLE*}$ and $R_{S-SAMPLE}$ exceeds the corresponding predetermined threshold, the method can determine that $R_{S-SAMPLE*}$ does not conform with $R_{S-SAMPLE}$ and that the anomaly in the operation of the chromatography system originates at least partly from the sample handling unit. If the deviation, if any, between $R_{S-SEP*}$ and $R_{S-SEP}$ exceeds the corresponding predetermined threshold, the method can determine that $R_{S-SEP*}$ does not conform with $R_{S-SEP}$ and that the anomaly in the operation of the chromatography system originates at least partly from the chromatographic separation unit. If the deviation, if any, between $R_{S-DET*}$ and $R_{S-DET}$ exceeds the corresponding predetermined threshold, the method can determine that $R_{S-DET*}$ does not conform with $R_{S-DET}$ and that the anomaly in the operation of the chromatography system originates at least partly from the detection unit.

It is appreciated that depending on the application, the method can involve determining one, some, or all of the expected specific standard responses $R_{S-SAMPLE}$, $R_{S-SEP}$, and $R_{S-DET}$, determining one, some, or all of the current specific standard responses $R_{S-SAMPLE*}$, $R_{S-SEP*}$, and $R_{S-DET*}$, and assessing whether one, some, or all of the current specific standard responses $R_{S-SAMPLE*}$, $R_{S-SEP*}$, and $R_{S-DET*}$ conform with their respective expected specific standard responses $R_{S-SAMPLE}$, $R_{S-SEP}$, and $R_{S-DET}$.

In some embodiments, the method can assess whether the current specific standard responses $R_{S-SAMPLE*}$, $R_{S-SEP*}$, and $R_{S-DET*}$ conform with their respective expected specific standard responses $R_{S-SAMPLE}$, $R_{S-SEP}$, and $R_{S-DET}$ in a sequential manner. For example, the method may begin by assessing whether the current specific standard response $R_{S-DET*}$ associated with the detection unit 108 conforms with the expected specific standard responses $R_{S-DET}$. If $R_{S-DET*}$ does not conform with $R_{S-DET}$, the method may determine that the cause of the anomaly is at least partly related to the operation of the detection unit 108, and the anomaly detection and diagnostic operation may be ended. However, if $R_{S-DET*}$ does conform with $R_{S-DET}$, the method may determine that the cause of the anomaly is not related to the operation of the detection unit 108, and the method may continue by assessing whether the current specific standard response $R_{S-SAMPLE*}$ associated with the sample handling unit 102 conforms with the expected specific standard responses $R_{S-SAMPLE}$. If $R_{S-SAMPLE*}$ does not conform with $R_{S-SAMPLE}$, the method may determine that the cause of the anomaly is at least partly related to the operation of the sample handling unit 102, and the anomaly detection and diagnostic operation may be ended. However, if $R_{S-SAMPLE*}$ does conform with $R_{S-SAMPLE}$, the method may determine that the cause of the anomaly is not related to the operation of the sample handling unit 102, and the method may continue by assessing whether the current specific standard response $R_{S\text{-}SEP*}$ associated with the chromatographic separation unit 106 conforms with the expected specific standard responses $R_{S\text{-}SEP}$. If $R_{S\text{-}SEP*}$ does not conform with $R_{S\text{-}SEP}$, the method may determine that the cause of the anomaly is at least partly related to the operation of the chromatographic separation unit 106, and the anomaly detection and diagnostic operation may be ended. However, if $R_{S\text{-}SEP*}$ does conform with $R_{S\text{-}SEP}$, the method may determine that the cause of the anomaly is not related to the operation of the chromatographic separation unit 106, and the anomaly detection and diagnostic operation may be ended.

Based on the outcome of the diagnosis operation, the method can include a step of generating an alert. The alert can be an audible alert, a visual signal, a tactile alert, a vibrational alert, or any combination thereof. The chromatography system can include an output device for generating the alert and/or be configured to transmit the alert to an external device (e.g., an operator's mobile device) using wired and/or wireless communication links. The alert can include a request or a recommendation to perform one or more actions. Non-limiting examples of such actions may be related to maintenance, cleaning, repair, replacement, inspection, testing, recalibration, change of operating regime, or any combination thereof.

In some embodiments, in addition to or instead of generating an alert, the method can include a step of taking a corrective action in order to attempt to compensate for the anomaly. Depending on the application, the chromatography system may be configured to implement the corrective action automatically, possibly in real-time, or only upon user authorization. It is appreciated that various types of corrective actions may be recommended, requested, or performed. For example, in some embodiments, if it is determined that the detected anomaly originates at least partly from the sample handling unit and is indicative of insufficient injection volume, the corrective action can include a step of increasing the sample concentration time. In some embodiments, if it is determined that the detected anomaly originates at least partly from the detection unit, the corrective action can include a step of adjusting (typically increasing) the sensitivity of the detector to help overcome the issue. In some embodiments, the method can include a step of verifying the effect of the corrective action on the operation of the chromatography system. The verification can include a step of determining a corrected overall standard response using the same or another test sample, and assessing whether the deviation between the corrected overall standard response and the expected overall standard response is less than the predetermined threshold.

As will now be described, the present techniques can implement other methods for validating the operation of a chromatography system in an attempt to improve its reliability and prevent faulty analysis.

Figure 6:
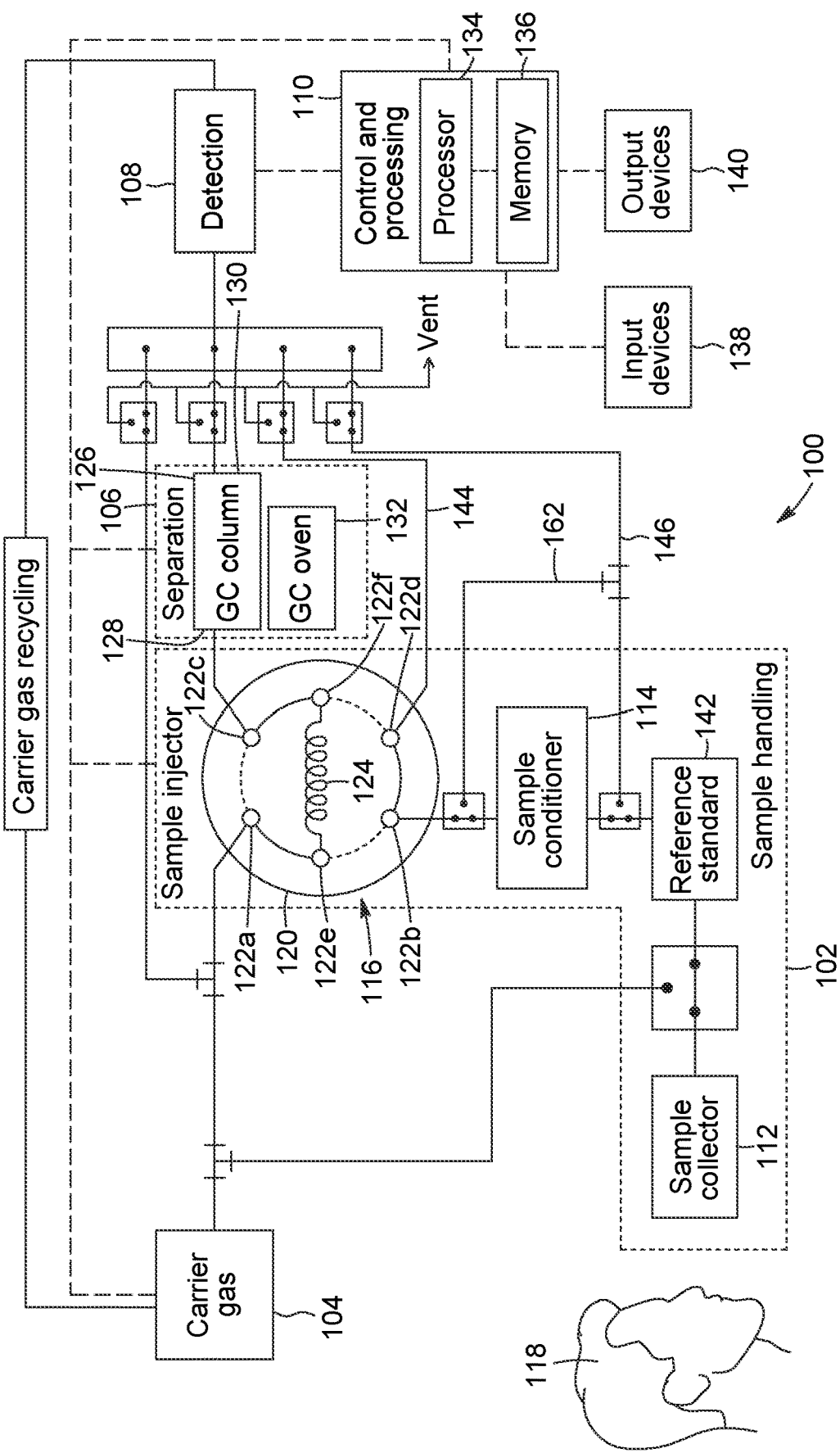
FIG. 6 is a schematic representation of another possible embodiment of a GC system.

Referring to FIG. 6, there is illustrated another embodiment of a GC system 100. The embodiment of FIG. 6 shares several features with the embodiment of FIG. 1, which will not be described again other than to highlight differences between them. The GC system 100 generally includes a sample handling unit 102, a carrier gas unit 104, a chromatographic separation unit 106, a detection unit 108, and a control and processing unit 110, which can be similar to those of FIG. 1. To further improve its robustness and autonomy, the GC system 100 of FIG. 6 includes a carrier gas recycling unit 148 for recycling the carrier gas, certifying its quality, and reducing its consumption.

The provision of the carrier gas recycling unit 148 can allow for the GC system 100 to remain in standby for a longer period of time. This is because, between analyses, the vented carrier gas would be recycled back into the carrier gas unit 104 instead of being vented to atmosphere and wasted. In some embodiments, the carrier gas recycling unit 148 can include a noble gas purifier, which can be provided with an integrated end-of-life detector configured for assessing the quality of the purified carrier gas.

It is appreciated that over time, chromatographic components may fail, start leaking, and become polluted. For example, pollutants may contaminate the chromatographic column. In some implementations, an optional step may be included in the present techniques to monitor, continuously or intermittently, the presence and level of some specific pollutants. Non-limiting examples of possible pollutants include, to name a few, $N_2$, $O_2$, and $H_2O$. When a measured pollutant level exceeds a predetermined threshold, an alert may be generated to recommend or request cleaning of the chromatography system.

Figure 7:
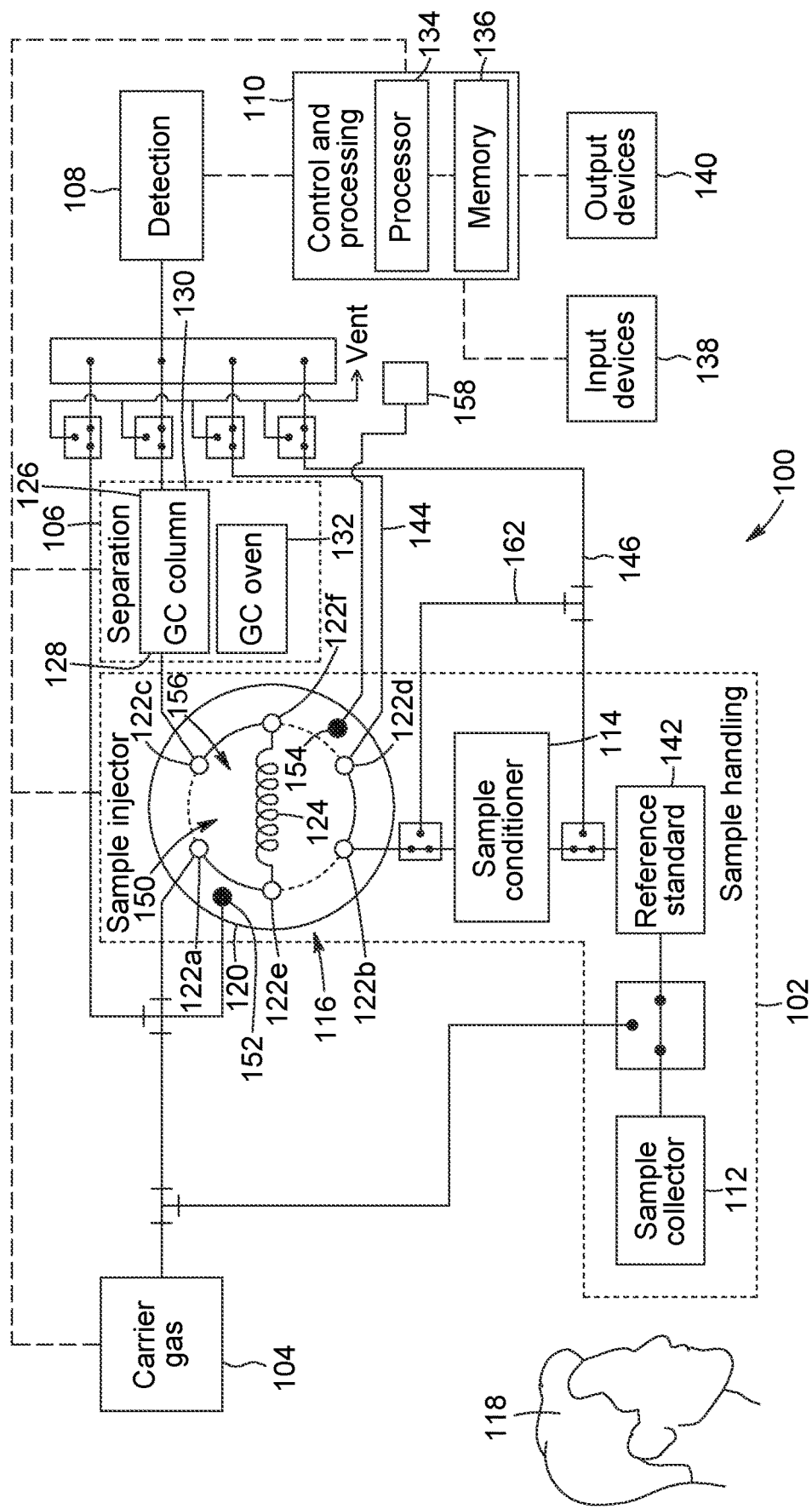
FIG. 7 is a schematic representation of another possible embodiment of a GC system.

Referring to FIG. 7, there is illustrated another embodiment of a GC system 100. The embodiment of FIG. 7 shares several features with the embodiment of FIG. 1, which will not be described again other than to highlight differences between them. The GC system 100 generally includes a sample handling unit 102, a carrier gas unit 104, a chromatographic separation unit 106, a detection unit 108, and a control and processing unit 110, which can be similar to those of FIG. 1. In particular, as in FIG. 1, the sample handling unit 102 includes a sample injector 116 having a multiport switching valve 120. The GC system 100 of FIG. 7 may be configured to implement a method including steps of circulating purge gas through the sample injector 116; detecting the purge gas after the purge gas exits the sample injector 116, generating, from the detected purge gas, a purge gas detection signal; analyzing the purge gas detection signal to assess whether the purge gas detection signal includes a feature indicative of a presence of contaminants in the detected purge gas; and if the purge gas detection signal includes such a feature, determining that a leak integrity of the sample injector 116 is possibly compromised.

In FIG. 7, the multiport switching valve 120 can include a purge system 150 having a purge inlet 152, a purge outlet 154, and a purge channel 156. The purge inlet 152 is connected to the carrier gas unit 104 for receiving carrier gas therefrom for use as purge gas for cleaning the interior of the multiport switching valve 120. The purge outlet 154 is connected to a purge gas detector 158 configured to detect the purge gas after the purge gas has passed through the purge system 150 and generate, from the detected purge gas, a purge gas detection signal that conveys information on the composition of the purge gas. In FIG. 7, the purge gas detector 158 is a detector separate from the detection unit 108. However, in other embodiments, the detection unit 108 can act as or include the purge gas detector 158. The purge gas detection signal can be analyzed for features indicative of the presence of contaminants in the purge gas, which can provide an indication of the presence of leaks in the ports of the multiport switching valve 120, through which contaminants can enter the purge system 150 and mix with the purge gas. When the level of contaminants detected in the purge gas exceeds a predetermined threshold, an alert may be generated to indicate that the leak integrity of the multiport switching valve 120 may be compromised.

Referring to FIG. 8, there is illustrated another embodiment of a GC system 100. The embodiment of FIG. 8 shares several features with the embodiment of FIG. 1, which will not be described again other than to highlight differences between them. The GC system 100 generally includes a sample handling unit 102, a carrier gas unit 104, a chromatographic separation unit 106, a detection unit 108, and a control and processing unit 110, which can be similar to those of FIG. 1. In FIG. 8, the sample conditioner 114 includes a sample trap 160 provided with a sorbent tube or material configured for sample concentration and separation from the sample matrix. The sample trap 160 is connected to ports 122e-122f of the multiport switching valve 120. It is appreciated the structure and operation of sample traps connected to multiport switching valves in GC applications are known in the art and need not be described in detail herein. A challenge in chromatography is the variability in injected sample volume. For example, variations in injected sample volume may be caused by an incorrect volume being circulated into the sorbent tube and/or a deterioration of the sorbent tube material. Uncontrolled variations in sample injection volume can impair the precision and accuracy of chromatography analysis. In some embodiments, the present techniques provide a method of calculating or assessing the injected sample volume.

A conventional approach to determining injected sample volume can involve measuring the sample flow going through the sorbent tube of the sample trap. While this approach may be acceptable in some instances, it does not provide a determination or confirmation that the correct sample volume has been injected. Rather than measuring the sample flow, the method according to the present techniques connects the sample vent 122d of the multiport switching valve 120 to the detection unit 108 via a suitable flow path 144. In other variants, a dedicated gas detector distinct from the detection unit 108 may be used for this purpose.

In the present method, a sample containing target analytes in a sample gas matrix is injected in the sample trap 160, which is provided with a sorbent tube or material. For example, in the case of an exhaled breath sample, the target analytes may include trace amounts of diagnostically useful VOCs and the sample gas matrix may consist of air. During sample injection, the sorbent tube extracts the target analytes from the sample gas matrix, thus allowing the analytes to be accumulated and concentrated inside the sample trap 160. The sample gas matrix is not retained by the sorbent tube and is released from the sample trap 160 via the sample vent 122d, where it is carried along the flow path 144 and into the detection unit 108. The detection unit 108 is configured to detect the sample gas matrix. The detected signal can include one or more peaks indicative of the composition of the sample matrix. For example, in applications such as exhaled breath analysis where the sample gas matrix is (or is primarily) air, the detected signal is expected to include a nitrogen peak. If it can be assumed that the detector response is specific and representative of nitrogen, the area of the nitrogen peak can be used to calculate or estimate the injected volume. Furthermore, when the sample matrix is (or is primarily) air, the presence of a nitrogen peak can provide confirmation that the correct sample volume has been injected.

Referring to FIG. 9, there is illustrated another embodiment of a GC system 100. The embodiment of FIG. 9 shares several features with the embodiment of FIG. 8, which will not be described again other than to highlight differences between them. As in FIG. 8, the sample conditioner 114 includes a sample trap 160 connected to ports 122e-122f of the multiport switching valve 120 and provided with a sorbent tube or material configured for sample extraction and concentration. The embodiment of FIG. 9 can be used to assess the leak integrity of the sample conditioner 114 and the concomitant risk of sample contamination. The embodiment of FIG. 9 can also be used to assess, for example, before performing a chromatography analysis, whether the sample conditioner 114 is back to known initial conditions.

In particular, the GC system 100 of FIG. 9 may be configured to implement a method including steps flowing purified gas through the sample conditioner 114, where the sample conditioner 114 is configured for conditioning the sample prior to injection of the sample into the chromatographic separation unit 106; detecting the purified gas after the purified gas exits the sample conditioner 114; generating, from the detected purified gas, a purified gas detection signal; analyzing the purified gas detection signal to assess whether the purified gas detection signal includes a feature indicative of a presence of contaminants in the detected purified gas; and if the purified gas detection signal includes such a feature, determining that a leak integrity of the sample conditioner 114 is possibly compromised.

In FIG. 9, in order to assess leak integrity, the sample vent 122d of the multiport switching valve 120 is connected to the detection unit 108 via a suitable flow path 144. Alternatively, a dedicated gas detector may be used instead of the detection unit 108. The method involves using the detection unit 108 to measure trace amounts of molecules, such as $N_2$ and $O_2$, in a purified flow of gas, such as argon or helium, after the purified gas has flown through the sample conditioner 114. The presence of molecules such as $N_2$ and $O_2$ can be indicative of an issue with the leak integrity of the sample conditioner 114. In FIG. 9, the purified flow of gas is supplied by the carrier gas unit 104. In some embodiments, the method can include a purge step to clean the sample conditioner 114, typically by heating it at high temperature over a period of time. When the GC system 100 is used to analyze exhaled breath samples or other gas samples containing air, high moisture concentrations can be reached. As can be appreciated, moisture can stick to and degrade the sorbent tube, thus affecting the performance of the GC system 100. By connecting the detection unit 108 to the sample vent 122d, trace amounts of water vapor or other compounds can be detected and quantified.

In accordance with another aspect, there is provided a non-transitory computer readable storage medium having stored thereon computer readable instructions that, when executed by a processor, cause the processor to perform a method for anomaly detection and diagnosis in a chromatography system configured for obtaining a chromatogram of a sample including a known quantity of a reference standard. The chromatography system can include a sample handling unit, a chromatographic separation unit, and a detection unit. The method may include providing the chromatogram of the sample, determining peak information corresponding to the reference standard in the chromatogram of the sample, and determining whether the peak information conforms with an expected overall standard response of the chromatography system associated with the reference standard. If it is determined that the peak information conforms with the expected overall standard response, the method may include determining that there is no anomaly in the operation of the chromatography system. However, if it is determined that the peak information does not conform with the expected overall standard response, the method may include determining that there is an anomaly in the operation of the chromatography system and diagnosing a cause of the anomaly as relating to at least one of the operation of the sample handling unit, the operation of the chromatographic separation unit, and the operation of the detection unit. It is appreciated that the method performed by the processor may include various steps, aspects, and features of the anomaly detection and diagnosis method described herein.

In accordance with another aspect, there is provided a computer device including a processor and a non-transitory computer readable storage medium operatively coupled to the processor and having stored thereon computer readable instructions that, when executed by a processor, cause the processor to perform various steps of the anomaly detection and diagnosis method described herein. FIG. 1 depicts an example of a computer device 110 (also referred to above as a control and processing unit) that includes a processor 134 and a non-transitory computer readable storage medium 136 (also referred to above as a memory) operably connected to the processor 134.

Numerous modifications could be made to the embodiments described above without departing from the scope of the appended claims.

The invention claimed is:

1. A method for anomaly detection and diagnosis in a chromatography system, the chromatography system comprising a sample handling unit, a chromatographic separation unit, and a detection unit, the method comprising:
   performing, with the chromatography system, a chromatography analysis of a sample to obtain a chromatogram of the sample, the sample comprising a known quantity of a reference standard;
   determining peak information corresponding to the reference standard in the chromatogram of the sample;
   determining whether the peak information conforms with an expected overall standard response of the chromatography system associated with the reference standard;
   if it is determined that the peak information conforms with the expected overall standard response, determining that there is no anomaly in the operation of the chromatography system; and
   if it is determined that the peak information does not conform with the expected overall standard response, determining that there is an anomaly in the operation of the chromatography system and diagnosing a cause of the anomaly as relating to at least one of the operation of the sample handling unit, the operation of the chromatographic separation unit, and the operation of the detection unit.

2. The method of claim 1, further comprising a precalibration operation of determining the expected overall standard response.

3. The method of claim 1, wherein determining whether the peak information conforms with the expected overall standard response comprises:
   determining, from the peak information, a current overall standard response of the chromatography system associated with the reference standard; and
   assessing whether the current overall standard response deviates from the expected overall standard response by more than a predetermined threshold.

4. The method of claim 1, wherein diagnosing the cause of the anomaly comprises performing at least one of the following three assessment operations:
   assessing whether a first current specific standard response of the chromatography system associated with the reference standard and conveying information about the operation of the sample handling unit conforms with a first expected specific standard response associated with the sample handling unit, and if not, determining that the cause of the anomaly is at least partly related to the operation of the sample handling unit;
   assessing whether a second current response of the chromatography system associated with the reference standard and conveying information about the operation of the chromatographic separation unit conforms with a second expected specific standard response associated with the chromatographic separation unit, and if not, determining that the cause of the anomaly is at least partly related to the operation of the chromatographic separation unit; and
   assessing whether a third current response of the chromatography system associated with the reference standard and conveying information about the operation of the detection unit conforms with a third expected specific standard response associated with the detection unit, and if not, determining that the cause of the anomaly is at least partly related to the operation of the detection unit.

5. The method of claim 4, further comprising a precalibration operation of determining at least one of the first, second, and third expected specific standard responses.

6. The method of claim 4, wherein assessing whether each of the first, second, and third current responses of the chromatography system conforms with a respective one of the first, second, and third expected specific standard responses comprises performing a comparison operation based on a respective predetermined threshold.

7. The method of claim 4, wherein performing at least one of the assessment operations comprises performing all of the three assessment operations.

8. The method of claim 1, wherein the reference standard is an internal standard.

9. The method of claim 1, wherein the sample containing the known quantity of the reference standard is a test sample comprising target analytes.

10. The method of claim 9, further comprising adding the reference standard to the test sample prior to performing the chromatography analysis.

11. The method of claim 10, wherein the target analytes are provided in a sample gas matrix, and wherein the method further comprises:
   receiving the test sample in a sample trap of the sample handling unit configured for accumulating and concentrating the test sample prior to injection of the test sample into the chromatographic separation unit;
   releasing the sample gas matrix from the sample trap;
   detecting the sample gas matrix released from the sample trap and generating therefrom a detection signal; and
   analyzing the detection signal to determine information conveying a volume of the test sample injected into the chromatographic separation unit.

12. The method of claim 9, wherein the test sample is an exhaled breath sample.

13. The method of claim 9, further comprising analyzing the chromatogram of the sample to perform identification and quantification of the target analytes.

14. The method of claim 1, wherein the sample containing the known quantity of the reference standard is a standard sample, and wherein the method further comprises:
   performing, with the chromatography system, and before or after the chromatography analysis of the standard sample, a chromatography analysis of a test sample to obtain a chromatogram of the test sample, the test sample comprising target analytes; and analyzing the chromatogram of the test sample to perform identification and quantification of the target analytes.

15. The method of claim 14, wherein the reference standard has a same composition as one of the target analytes of the test sample.

16. The method of claim 14, wherein the test sample is an exhaled breath sample.

17. The method of claim 16, wherein the reference standard comprises benzene, styrene, toluene, hydrogen sulfide, or a combination thereof.

18. The method of claim 1, wherein the sample handling unit comprises a sample conditioner configured for conditioning the sample prior to injection of the sample into the chromatographic separation unit, and wherein the method further comprises:

flowing purified gas through the sample conditioner;

detecting the purified gas after the purified gas exits the sample conditioner;

generating, from the detected purified gas, a purified gas detection signal;

analyzing the purified gas detection signal to assess whether the purified gas detection signal comprises a feature indicative of a presence of contaminants in the detected purified gas; and if the purified gas detection signal comprises such a feature, determining that a leak integrity of the sample conditioner is possibly compromised.

19. The method of claim 1, further comprising taking a corrective action to correct, at least partly, the anomaly.

20. The method of claim 19, wherein:

if it is determined that the anomaly originates at least partly from the sample handling unit, applying the corrective action at least partly to the sample handling unit;

if it is determined that the anomaly originates at least partly from the chromatographic separation unit, applying the corrective action at least partly to the chromatographic separation unit; and if it is determined that the anomaly originates at least partly from the detection, applying the corrective action at least partly to the detection unit.

21. The method of claim 1, wherein the detection unit comprises a plasma emission detector.

22. The method of claim 1, wherein the chromatography system is a gas chromatography system, and the sample is a gas sample.

23. The method of claim 1, wherein the sample handling unit comprises a sample injector configured for injecting the sample into the chromatographic separation unit, and wherein the method further comprises:

circulating purge gas through the sample injector;

detecting the purge gas after the purge gas exits the sample injector;

generating, from the detected purge gas, a purge gas detection signal;

analyzing the purge gas detection signal to assess whether the purge gas detection signal comprises a feature indicative of a presence of contaminants in the detected purge gas; and if the purge gas detection signal comprises such a feature, determining that a leak integrity of the sample injector is possibly compromised.

24. A chromatography system for performing a chromatography analysis of a sample comprising a known quantity of a reference standard, the chromatography system comprising:

a sample handling unit configured to process the sample;

a chromatographic separation unit configured to receive the sample from the sample handling unit and to perform a chromatographic separation of the sample;

a detection unit configured to detect the chromatographically separated sample and generate therefrom a detection signal;

a control and processing unit configured to:

receive the detection signal from the detection unit;

obtain a chromatogram of the sample from the detection signal;

determine peak information corresponding to the reference standard in the chromatogram of the sample;

determine whether the peak information conforms with an expected overall standard response of the chromatography system associated with the reference standard;

if it is determined that the peak information conforms with the expected overall standard response, determine that there is no anomaly in the operation of the chromatography system; and if it is determined that the peak information does not conform with the expected overall standard response, determine that there is an anomaly in the operation of the chromatography system and diagnose a cause of the anomaly as relating to at least one of the operation of the sample handling unit, the operation of the chromatographic separation unit, and the operation of the detection unit.

25. The chromatography system of claim 24, wherein the control and processing unit is configured to determine whether the peak information conforms with the expected overall standard response by:

determining, from the peak information, a current overall standard response of the chromatography system associated with the reference standard; and assessing whether the current overall standard response deviates from the expected overall standard response by more than a predetermined threshold.

26. The chromatography system of claim 24, wherein the control and processing unit is configured to diagnose the cause of the anomaly by performing at least one of the following three assessment operations:

assessing whether a first current specific standard response of the chromatography system associated with the reference standard and conveying information about the operation of the sample handling unit conforms with a first expected specific standard response associated with the sample handling unit, and if not, determining that the cause of the anomaly is at least partly related to the operation of the sample handling unit;

assessing whether a second current response of the chromatography system associated with the reference standard and conveying information about the operation of the chromatographic separation unit conforms with a second expected specific standard response associated with the chromatographic separation unit, and if not, determining that the cause of the anomaly is at least partly related to the operation of the chromatographic separation unit; and assessing whether a third current response of the chromatography system associated with the reference standard and conveying information about the operation of the detection unit conforms with a third expected specific standard response associated with the detection unit, and if not, determining that the cause of the anomaly is at least partly related to the operation of the detection unit.

27. The chromatography system of claim 24, wherein the sample containing the known quantity of the reference standard is a test sample comprising target analytes, and wherein the sample handling unit comprises a sample collector configured to collect the test sample.

28. The chromatography system of claim 27, wherein the test sample is an exhaled breath sample, and wherein the sample collector is configured to receive the exhaled breath sample via exhalation by a user.

29. The chromatography system of claim 24, wherein the detection unit comprises a plasma emission detector.

30. The chromatography system of claim 24, wherein the chromatography system is a gas chromatography system.

31. The chromatography system of claim 30, further comprising a carrier gas unit configured to supplying a flow of carrier gas and introduce the flow of carrier gas with the gas sample to form a mobile phase for injection into the chromatographic separation unit.

32. A non-transitory computer readable storage medium having stored thereon computer readable instructions that, when executed by a processor, cause the processor to perform a method for anomaly detection and diagnosis in a chromatography system configured for obtaining a chromatogram of a sample comprising a known quantity of a reference standard, the chromatography system comprising a sample handling unit, a chromatographic separation unit, and a detection unit, the method comprising:
providing the chromatogram of the sample;
determining peak information corresponding to the reference standard in the chromatogram of the sample;
determining whether the peak information conforms with an expected overall standard response of the chromatography system associated with the reference standard;
if it is determined that the peak information conforms with the expected overall standard response, determining that there is no anomaly in the operation of the chromatography system; and
if it is determined that the peak information does not conform with the expected overall standard response, determining that there is an anomaly in the operation of the chromatography system and diagnosing a cause of the anomaly as relating to at least one of the operation of the sample handling unit, the operation of the chromatographic separation unit, and the operation of the detection unit.

33. The non-transitory computer readable storage medium of claim 32, wherein the method further comprises determining the expected overall standard response via a precalibration operation.

34. The non-transitory computer readable storage medium of claim 32, wherein determining whether the peak information conforms with the expected overall standard response comprises:
determining, from the peak information, a current overall standard response of the chromatography system associated with the reference standard; and
assessing whether the current overall standard response deviates from the expected overall standard response by more than a predetermined threshold.

35. The non-transitory computer readable storage medium of claim 32, wherein diagnosing the cause of the anomaly comprises performing at least one of the following three assessment operations:
assessing whether a first current specific standard response of the chromatography system associated with the reference standard and conveying information about the operation of the sample handling unit conforms with a first expected specific standard response associated with the sample handling unit, and if not, determining that the cause of the anomaly is at least partly related to the operation of the sample handling unit;
assessing whether a second current response of the chromatography system associated with the reference standard and conveying information about the operation of the chromatographic separation unit conforms with a second expected specific standard response associated with the chromatographic separation unit, and if not, determining that the cause of the anomaly is at least partly related to the operation of the chromatographic separation unit; and
assessing whether a third current response of the chromatography system associated with the reference standard and conveying information about the operation of the detection unit conforms with a third expected specific standard response associated with the detection unit, and if not, determining that the cause of the anomaly is at least partly related to the operation of the detection unit.

36. The non-transitory computer readable storage medium of claim 35, wherein the method further comprises determining at least one of the first, second, and third expected specific standard responses via a precalibration operation.

37. The non-transitory computer readable storage medium of claim 35, wherein assessing whether each of the first, second, and third current responses of the chromatography system conforms with a respective one of the first, second, and third expected specific standard responses comprises performing a comparison operation based on a respective predetermined threshold.

38. The non-transitory computer readable storage medium of claim 35, wherein the method further comprises determining a corrective action to correct, at least partly, the anomaly.

39. The non-transitory computer readable storage medium of claim 38, wherein:
if it is determined that the anomaly originates at least partly from the sample handling unit, the method comprises applying the corrective action at least partly to the sample handling unit;
if it is determined that the anomaly originates at least partly from the chromatographic separation unit, the method comprises applying the corrective action at least partly to the chromatographic separation unit; and
if it is determined that the anomaly originates at least partly from the detection, the method comprises applying the corrective action at least partly to the detection unit.

40. A computer device comprising:
a processor; and
the non-transitory computer readable storage medium of claim 32, the non-transitory computer readable storage medium being operatively coupled to the processor.

* * * * *